(12) United States Patent
Tobler et al.

(10) Patent No.: US 7,608,595 B2
(45) Date of Patent: Oct. 27, 2009

(54) 4"-DEOXY-4"-(S)-AMIDO AVERMECTIN DERIVATIVES

(75) Inventors: Hans Tobler, Basel (CH); Fiona Murphy Kessabi, Basel (CH)

(73) Assignee: Merial Limited, Duluth, GA (US)

( * ) Notice: Subject to any disclaimer, the term of this patent is extended or adjusted under 35 U.S.C. 154(b) by 588 days.

(21) Appl. No.: 10/513,247

(22) PCT Filed: May 6, 2003

(86) PCT No.: PCT/EP03/04740

§ 371 (c)(1),
(2), (4) Date: Nov. 2, 2004

(87) PCT Pub. No.: WO03/095468

PCT Pub. Date: Nov. 20, 2003

(65) Prior Publication Data

US 2005/0176656 A1  Aug. 11, 2005

(30) Foreign Application Priority Data

May 7, 2002  (CH)  ........................................ 774/02

(51) Int. Cl.
*A01N 43/04* (2006.01)
*A61K 31/70* (2006.01)
*C07H 17/08* (2006.01)

(52) U.S. Cl. .......................................... 514/28; 536/7.1
(58) Field of Classification Search .................... None
See application file for complete search history.

(56) References Cited

U.S. PATENT DOCUMENTS

| | | | | |
|---|---|---|---|---|
| 4,203,976 A | | 5/1980 | Fisher et al. | |
| 4,206,205 A | | 6/1980 | Mrozik et al. | |
| 4,427,663 A | * | 1/1984 | Mrozik | ......................... 514/30 |
| 4,622,313 A | | 11/1986 | Wyvrath, Jr. et al. | |
| 4,831,016 A | | 5/1989 | Mrozik et al. | |
| 4,895,837 A | | 1/1990 | Mrozik et al. | |
| 5,023,241 A | * | 6/1991 | Linn et al. | ..................... 514/30 |
| 5,057,499 A | | 10/1991 | Mrozik et al. | |
| 5,169,839 A | | 12/1992 | Linn et al. | |
| 5,192,546 A | | 3/1993 | Abercrombie et al. | |
| 5,208,222 A | | 5/1993 | Meinke et al. | |

(Continued)

FOREIGN PATENT DOCUMENTS

| | | |
|---|---|---|
| EP | 001688 | 5/1979 |
| EP | 0259688 | 3/1988 |
| EP | 0266131 | 5/1988 |
| EP | 0301806 | 2/1989 |
| EP | 0340849 | 11/1989 |
| EP | 0343708 | 11/1989 |
| EP | 0375393 | 6/1990 |
| EP | 0411897 | 6/1991 |
| EP | 0456509 | 11/1991 |
| EP | 0465121 | 1/1992 |

(Continued)

OTHER PUBLICATIONS

Shoop, et. al., International Journal for Parasitology (1996), 26(11), 1227-1235.*
J. Med. Chem. 1992, 35, 3879-3884; "Affinity Probes for the Avermectin Binding Proteins".
Bioorganic & Medicinal Chemistry Letter, vol. 5, No. 20, 2435-2440 (1995); "4"-Deoxy-4"-Aminoavermectins with Potent Broad Spectrum Antiparasitic Activities".

(Continued)

*Primary Examiner*—James O Wilson
*Assistant Examiner*—Jeffrey H Murray
(74) *Attorney, Agent, or Firm*—Judy Jarecki-Black; Merial Limited; Thomas Kowalski, Esq

(57) ABSTRACT

A compound of formula (I); that has the S-configuration at the 4"-position and wherein the bond between carbon atoms 22 and 23 is a single or a double bond; $R_1$ is $C_1$-$C_{12}$alkyl, $C_3$-$C_8$cycloalkyl; or $C_2$-$C_{12}$alkenyl; $R_2$ is H, or, for example, unsubstituted or mono- to penta-substituted $C_1$-$C_{12}$alkyl, $C_2$-$C_{12}$alkenyl, $C_2$-$C_{12}$alkynyl or $C_1$-$C_6$alkoxy-$C_1$-$C_6$alkyl; $R_3$ is H or, for example, $C_1$-$C_{12}$alkyl; X is a bond, O, $NR_4$ or S; and Z is C=O, C=S or $SO_2$; and, where applicable, E/Z isomers, mixtures of E/Z isomers and/or tautomers, in each case in free form or in salt form; a process for the preparation of and the use of those compounds and their isomers and tautomers; starting materials for the preparation of the compounds of formula (I); pesticidal compositions in which the active ingredient has been selected from those compounds and their tautomers; and a method of controlling pests using those compositions are described.

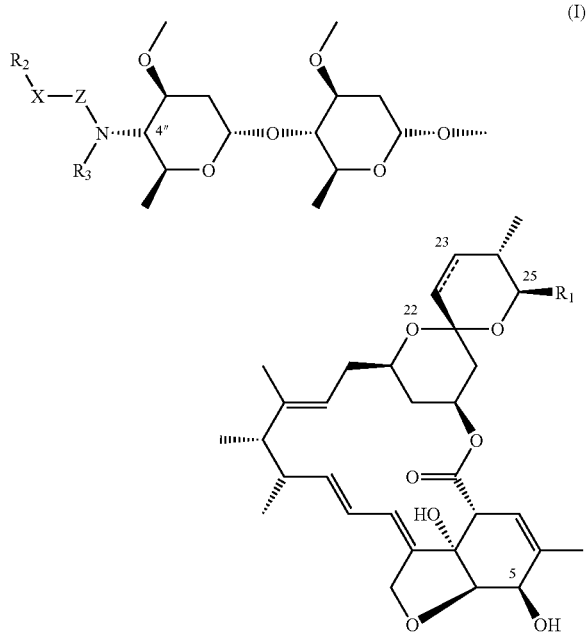

5 Claims, No Drawings

U.S. PATENT DOCUMENTS

| | | | |
|---|---|---|---|
| 5,229,415 A | 7/1993 | Linn et al. | |
| 5,346,698 A | 9/1994 | Abercrombie et al. | |
| 5,362,863 A | 11/1994 | Cvetovich et al. | |
| 5,436,355 A | 7/1995 | Demchak et al. | |
| 5,606,057 A | 2/1997 | Pitterna et al. | |
| 5,945,445 A | 8/1999 | Barringer et al. | |
| 5,981,500 A | 11/1999 | Bishop et al. | |
| 6,605,595 B1 | 8/2003 | Omura et al. | |
| 6,875,727 B2 | 4/2005 | Hofer et al. | |
| 6,933,260 B2 | 8/2005 | Cassayre et al. | |
| 7,250,402 B2 | 7/2007 | Omura et al. | |
| 7,378,399 B2 | 5/2008 | Cassayre et al. | |
| 2006/0140997 A1 | 6/2006 | Pitterna et al. | |
| 2006/0205595 A1* | 9/2006 | Pitterna et al. | 504/100 |
| 2008/0051353 A1 | 2/2008 | Jung et al. | |

FOREIGN PATENT DOCUMENTS

| | | |
|---|---|---|
| EP | 0506331 A | 9/1992 |
| EP | 0519731 | 12/1992 |
| EP | 0089202 | 9/2001 |
| EP | 1160252 A | 12/2001 |
| WO | WO 93/15099 | 8/1993 |
| WO | WO 95/20877 | 8/1995 |
| WO | WO 96/22300 A1 | 7/1996 |
| WO | 02068441 | 9/2002 |
| WO | WO 02/068442 | 9/2002 |
| WO | 03020738 | 3/2003 |
| WO | 03053988 | 7/2003 |
| WO | WO 2004/067534 | 8/2004 |

OTHER PUBLICATIONS

U.S. Appl. No. 10/568,715, filed Feb. 17, 2006, Kasaba et al.
U.S. Appl. No. 10/560,390, filed Mar. 22, 2006, Pitterna et al.
U.S. Appl. No. 10/544,274, filed Aug. 3, 2005, Cassayre et al.
U.S. Appl. No. 10/544,281, filed Aug. 3, 2005, Quaranta et al.
U.S. Appl. No. 10/543,638, filed Jul. 28, 2005, Pitterna et al.
U.S. Appl. No. 10/543/,643, filed Apr. 5, 2006, Pitterna et al.
U.S. Appl. No. 10/498,858, filed Jun. 14, 2004, Cassayre et al.
U.S. Appl. No. 10/488,225, filed Feb. 26, 2004, Tobler et al.
U.S. Appl. No. 11/319,686, filed Dec. 28, 2005, Pitterna et al.
U.S. Appl. No. 11/319,687, filed Dec. 28, 2005, Pitterna et al.
U.S. Appl. No. 10/539,274, filed Mar. 9, 2006, Maienfisch et al.
Cvetovich et al., .J. Org. Chem., 1994, 59, pp. 7704-7708.
Fisher, American Chemical Society Symposium, 1997, vol. 658, Phytochemicals for Pest Control.
Jones, T K et al., "Synthesis and Biological Activity of 4a,4-Disubstituted Avermectins": Journal of Agriculture and Food Chemistry, 1994, (42) pp. 1786-1790.
Meinke et al;. "Synthesis of Avermectin B1-4'-4'a -Oxide: a Precursor to Potent Antihelmintic Agents". Biorganic Medicinal Chemistry Letters, vol. 2, 1992 p. 537.
Mrozic, H. et al., "Avermectin Acyl Derivatives with Anti Helmintic Activity" Journal of Medicinal Chemistry, vol. 25, 1982, pp. 658-663.
Shoop et al Efficacy in Sheep and Pharmacokinetics in Cattle that led to the Selection of Epinomectin as a Topical Endectocide for Cattle, International Journal for Parasitology, 1996, 26 (11), 1227-1235.
Wrzesinski et al., Journal of Agricultural and Food Chemistry, vol. 44, 1996. pp. 304-312.

* cited by examiner

4"-DEOXY-4"-(S)-AMIDO AVERMECTIN DERIVATIVES

This application is a 371 of International Application No. PCT/EP03/04740 filed May 6, 2003, which claims priority to CH 774/02, filed May 7, 2002, the contents of which are incorporated herein by reference.

The invention relates to (1) a compound of formula

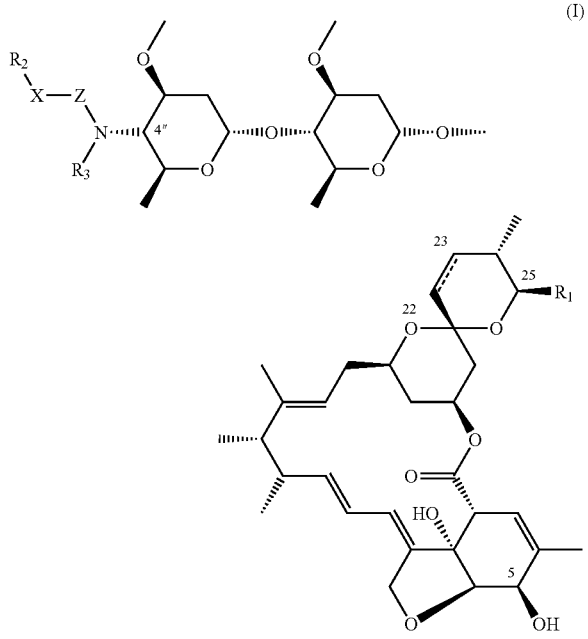

(I)

that has the S-configuration at the 4"-position and wherein the bond between carbon atoms 22 and 23 is a single or a double bond;

$R_1$ is $C_1$-$C_{12}$alkyl, $C_3$-$C_8$acycloalkyl; or $C_2$-$C_{12}$alkenyl;

$R_2$ is H, $C_1$-$C_{12}$alkyl, $C_2$-$C_{12}$alkenyl, $C_2$-$C_{12}$alkynyl, $C_1$-$C_6$alkoxy-$C_1$-$C_6$alkyl, $C_3$-$C_8$cycloalkyl, —C(=O)—$R_5$, aryl or heteroaryl; wherein the $C_1$-$C_{12}$alkyl, $C_2$-$C_{12}$alkenyl, $C_2$-$C_{12}$alkynyl, $C_1$-$C_6$alkoxy-$C_1$-$C_6$alkyl, $C_3$-$C_8$cycloalkyl, aryl and heteroaryl substituents may be unsubstituted or mono- to penta-substituted;

$R_3$ is H, $C_1$-$C_{12}$alkyl, $C_3$-$C_{12}$cycloalkyl, $C_2$-$C_{12}$alkenyl or $C_2$-$C_{12}$alkynyl; wherein the $C_1$-$C_{12}$alkyl, $C_3$-$C_{12}$cycloalkyl, $C_2$-$C_{12}$alkenyl and $C_2$-$C_{12}$alkynyl substituents may be unsubstituted or mono- to penta-substituted;

X is a bond, O, $NR_4$ or S;

Z is C=O, C=S or $SO_2$;

$R_4$ is H, $C_1$-$C_8$alkyl, $C_3$-$C_8$cycloalkyl, $C_2$-$C_8$alkenyl, $C_2$-$C_8$alkynyl, benzyl or —C(=O)—$R_5$; or $R_2$ and $R_4$ together are a three- to seven membered alkylene or alkenylene bridge, wherein the alkylene or alkenylene bridges are unsubstituted or mono to tri-substituted; and wherein one of the methylene groups of the three- to seven membered alkylene- or alkenylene-bridge may be replaced by O, NH, S, S(=O) or $SO_2$; and wherein the substituents of the mentioned alkyl, alkenyl, alkynyl, cycloalkyl, alkylene, alkenylene, aryl and heteroaryl radicals as defined under $R_2$, $R_3$ and $R_4$ are selected from the group consisting of OH, =O, halogen, halo-$C_1$-$C_2$alkyl, CN, $NO_2$, —$N_3$, $C_3$-$C_8$cycloalkyl that is unsubstituted or substituted by from one to three methyl groups; norbornylenyl; $C_3$-$C_8$cycloalkenyl that is unsubstituted or substituted by from one to three methyl groups; $C_3$-$C_8$halo-cycloalkyl, $C_1$-$C_{12}$alkoxy, $C_1$-$C_6$alkoxy-$C_1$-$C_6$alkyl, $C_3$-$C_8$cycloalkoxy, $C_1$-$C_{12}$haloalkoxy, $C_1$-$C_{12}$alkylthio, $C_3$-$C_8$cycloalkylthio, $C_1$-$C_{12}$haloalkylthio, $C_1$-$C_{12}$alkylsulfinyl, $C_3$-$C_8$cycloalkylsulfinyl, $C_1$-$C_{12}$haloalkylsulfinyl, $C_3$-$C_8$halocycloalkylsulfinyl, $C_1$-$C_{12}$alkylsulfonyl, $C_3$-$C_8$cycloalkylsulfonyl, $C_1$-$C_{12}$haloalkylsulfonyl, $C_3$-$C_8$halocycloalkylsulfonyl, $C_2$-$C_8$alkenyl, $C_2$-$C_8$alkynyl, $NH(C_1$-$C_6$alkyl), —$N(C_1$-$C_6$alkyl)$_2$, —C(=O)$R_5$, —NHC(=O)$R_6$, =NO—$C_1$-$C_6$alkyl, —P(=O)(O$C_1$-$C_6$alkyl)$_2$; aryl, heterocyclyl, aryloxy, heterocyclyloxy; and aryl, heterocyclyl, aryloxy and heterocyclyloxy that, depending upon the possibilities of substitution at the ring, are mono- to penta-substituted by substituents selected from the group consisting of OH, =O, halogen, CN, $NO_2$, —$N_3$, $C_1$-$C_{12}$alkyl, $C_3$-$C_8$cycloalkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_6$alkoxy-$C_1$-$C_6$alkyl, dimethyl-amino-$C_1$-$C_6$alkoxy, $C_2$-$C_8$alkenyl, $C_2$-$C_8$alkynyl, phenoxy and phenyl-$C_1$-$C_6$alkyl; phenoxy that is unsubstituted or substituted by from one to three substituents selected independently of one another from halogen, methoxy, trifluoromethyl and trifluoromethoxy; phenyl-$C_1$-$C_6$alkoxy that is unsubstituted or substituted in the aromatic ring by from one to three substituents selected independently of one another from halogen, methoxy, trifluoromethyl and trifluoromethoxy; phenyl-$C_2$-$C_6$alkenyl, phenyl-$C_2$-$C_6$alkynyl, methylenedioxy, —C(=O)$R_5$, —O—C(=O)$R_6$, —NH—C(=O)$R_6$, $NH_2$, $NH(C_1$-$C_{12}$alkyl), $N(C_1$-$C_{12}$alkyl)$_2$, $C_1$-$C_6$alkylsulfinyl, $C_3$-$C_8$cycloalkylsulfinyl, $C_1$-$C_6$haloalkylsulfinyl, $C_3$-$C_8$halocycloalkylsulfinyl, $C_1$-$C_6$alkylsulfonyl, $C_3$-$C_8$cycloalkylsulfonyl, $C_1$-$C_6$haloalkylsulfonyl and $C_3$-$C_8$halocycloalkylsulfonyl;

$R_5$ is H, OH, SH, $NH_2$, $NH(C_1$-$C_{12}$alkyl), $N(C_1$-$C_{12}$alkyl)$_2$, $C_1$-$C_{12}$alkyl, $C_3$-$C_8$cycloalkyl $C_1$-$C_{12}$haloalkyl, $C_1$-$C_{12}$alkoxy, $C_1$-$C_{12}$haloalkoxy, $C_1$-$C_6$alkoxy-$C_1$-$C_6$alkoxy, $C_1$-$C_{12}$alkylthio, $C_2$-$C_8$alkenyloxy, $C_2$-$C_8$alkynyloxy; phenyl, phenoxy, benzyloxy, NH-phenyl, —$N(C_1$-$C_6$alkyl)-phenyl, NH—$C_1$-$C_6$alkyl-C(=O)—$R_7$, —$N(C_1$-$C_6$alkyl)-$C_1$-$C_6$alkyl-C(=O)—$R_7$; or phenyl, phenoxy, benzyloxy, NH-phenyl or —$N(C_1$-$C_6$alkyl)-phenyl each of which is substituted in the aromatic ring by from one to three substituents selected independently of one another from halogen, $C_1$-$C_6$alkoxy, $C_1$-$C_6$haloalkyl and $C_1$-$C_6$haloalkoxy;

$R_6$ is H, $C_1$-$C_{12}$alkyl, $C_1$-$C_{12}$haloalkyl, $C_2$-$C_8$alkenyl, $C_2$-$C_8$alkynyl, phenyl, benzyl, $NH_2$, $NH(C_1$-$C_{12}$alkyl), $N(C_1$-$C_{12}$alkyl)$_2$, —NH-phenyl or —$N(C_1$-$C_{12}$alkyl)-phenyl; and $R_7$ is H, OH, $C_1$-$C_{12}$alkyl, $C_1$-$C_{12}$alkoxy, $C_1$-$C_6$alkoxy-$C_1$-$C_6$alkoxy, $C_2$-$C_8$alkenyloxy, phenyl, phenoxy, benzyloxy, $NH_2$, $NH(C_1$-$C_{12}$alkyl), $N(C_1$-$C_{12}$alkyl)$_2$, —NH-phenyl or —$N(C_1$-$C_{12}$alkyl)-phenyl;

and, where applicable, to E/Z isomers, mixtures of E/Z isomers and/or tautomers, in each case in free form or in salt form;

with the proviso that Z is not C=O when X is a bond, $R_2$ is $CH_3$ or 2-aminoethyl, $R_3$ is hydrogen, the bond between carbon atoms 22 and 23 is a double bond and $R_1$ is i-propyl or sec-butyl;

to a process for the preparation of and to the use of those compounds and their isomers and tautomers; to starting materials for the preparation of the compounds of formula (I); to pesticidal compositions in which the active ingredient has been selected from the compounds of formula (I) and their tautomers; and to a method of controlling pests using those compositions.

Certain macrolide compounds are proposed for pest control in the literature. The biological properties of those known compounds are not entirely satisfactory, however, for which reason there is a need to provide further compounds having pesticidal properties, especially for the control of insects and members of the order Acarina. That problem is solved according to the invention by the provision of the present compounds of formula (I) wherein, at the 4"-position, the S-configuration is present.

The compounds claimed according to the invention are derivatives of avermectin. Avermectins are known to the person skilled in the art. They are a group of structurally closely related pesticidally active compounds which are obtained by fermentation of a strain of the microorganism *Streptomyces avermitilis*. Derivatives of avermectins can be obtained via conventional chemical syntheses.

The avermectins obtainable from *Streptomyces avermitilis* are designated A1a, A1b, A2a, A2b, B1a, B1b, B2a and B2b. Compounds with the designation "A" have a methoxy radical in the 5-position; those compounds designated "B" have an OH group. The "a" series comprises compounds wherein the substituent $R_1$ (in position 25) is a sec-butyl radical; in the "b" series there is an isopropyl radical in the 25-position. The number 1 in the name of a compound indicates that atoms 22 and 23 are bonded by a double bond; the number 2 indicates that they are bonded by a single bond and carbon atom 23 carries an OH group. The above designations are retained in the description of the present invention in order in the case of the non-natural avermectin derivatives according to the invention to indicate the specific structural type corresponding to natural avermectin. There are claimed according to the invention derivatives of compounds of the B1 series and related compounds having a single bond between carbon atoms 22 and 23 as well as compounds having other substituents such as cyclohexyl or 1-methylbutyl in the position $R_1$, more especially mixtures of derivatives of avermectin $B_1a$ and $B_1b$ in which, at the 4"-position, the S configuration is present.

Some of the compounds of formula (I) may be in the form of tautomers. Accordingly, any reference to the compounds of formula (I) hereinbefore and hereinafter is to be understood, where applicable, as including also corresponding tautomers, even if the latter are not specifically mentioned in every case.

The compounds of formula (I) and, where applicable, their tautomers can form salts, for example acid addition salts. These acid addition salts are formed, for example, with strong inorganic acids, such as mineral acids, for example sulfuric acid, a phosphoric acid or a hydrohalic acid, with strong organic carboxylic acids, such as unsubstituted or substituted, for example halo-substituted, $C_1$-$C_4$alkanecarboxylic acids, unsaturated or saturated dicarboxylic acids, or hydroxycarboxylic acids; or with organic sulfonic acids, such as unsubstituted or substituted, for example halo-substituted, $C_1$-$C_4$alkane- or aryl-sulfonic acids. Compounds of formula (I) that have at least one acidic group can furthermore form salts with bases. Suitable salts with bases are, for example, metal salts, such as alkali metal salts or alkaline earth metal salts, for example sodium, potassium or magnesium salts, or salts with ammonia or with an organic amine, such as morpholine, piperidine, pyrrolidine, a mono-, di- or tri-lower alkylamine, for example ethylamine, diethylamine, triethylamine or dimethylpropylamine, or a mono-, di- or tri-hydroxy-lower alkylamine, for example mono-, di- or triethanolamine. Corresponding internal salts may also be formed where appropriate. The free form is preferred. Among the salts of the compounds of formula (I), the agrochemically advantageous salts are preferred. Hereinbefore and hereinafter, any reference to the free compounds of formula (I) or their salts is to be understood as including, where appropriate, also the corresponding salts or the free compounds of formula (I), respectively. The same applies to tautomers of compounds of formula (I) and salts thereof.

Preferred anions of salts of compounds of formula (I) are:
the anion of a mineral acid, such as, for example, sulfuric acid, a phosphoric acid or a hydrohalic acid;

the anion of an organic carboxylic acid, such as an unsubstituted or substituted, for example halo-substituted, $C_1$-$C_4$alkanecarboxylic acid, an unsaturated or saturated dicarboxylic acid, or a hydroxycarboxylic acid;

the anion of an organic sulfonic acid, such as an unsubstituted or substituted, for example halo-substituted, $C_1$-$C_4$alkane- or aryl-sulfonic acid; or the anion of a C—H-active compound. These C—H-active compounds include especially organic compounds carrying strongly electron-attracting substituents, such as nitriles, carbonyls or nitro groups. Preference is given especially to anions of compounds of the formula $Y_1$—$CH_2$—$Y_2$, wherein $Y_1$ and $Y_2$ each represents an electron-attracting group. Preference is given more especially to the anions of malodinitrile, cyanoacetic acid, esters of cyanoacetic acid, amides of cyanoacetic acid, acetoacetic acid, esters of acetoacetic acid, acetyl acetone, cyanoacetone and barbituric acid; or the anion of an acid phenol, such as, for example, picric acid.

Preference is given most especially to 1:1 salts of compounds of formula (I) with the following acids: benzoic acid, maleic acid, fumaric acid, 2-hydroxybenzoic acid, salicylic acid, malic acid, benzenesulfonic acid, barbituric acid, 2-ethylbutyric acid, thiomalic acid, 3,5-dihydroxy-benzoic acid, trimesic acid, D-(−)-quinic acid, 2-bromo-benzoic acid, 2-phenyl-benzoic acid, 3,3'-thiodipropionic acid, naphthalene-1-carboxylic acid, 5-sulfosalicylic acid, 2-methoxy-phenylacetic acid, benzene-1,2,4-tricarboxylic acid, 3-hydroxy-benzoic acid, D-gluconic acid, 4,5-dichloro-phthalic acid, n-hexanoic acid (caproic acid), n-heptanoic acid (oenanthic acid), n-octanoic acid (caprylic acid), stearic acid, palmitic acid, 2,2'-dihydroxy-1,1'-dinaphthylmethane-3,3'-4, 4'-methylene-bis(3-hydroxy-2-naphthoic acid), embonic acid, 4-methoxy-phenylacetic acid (homoanisic acid), 2-anisic acid (2-methoxy-benzoic acid), adamantane-1-carboxylic acid, pyridine-3,4-dicarboxylic acid, 3,4-dihydroxy-benzoic acid, 1-hydroxy-2-naphthoic acid (1-naphthol-2-carboxylic acid), 2,2'-oxydiacetic acid (diglycolic acid), O-ethyl-glycolic acid, (2-naphthylthio)-acetic acid (S-(2-naphthyl)-thioglycolic acid), 2-naphthyloxy-acetic acid, perfluoro-octanoic acid, p-toluic acid, cyclohexanepropionic acid, 2,6-dihydroxypyridine-4-carboxylic acid (citrazinic acid), 3-methoxypropionic acid, 3,4,5-trihydroxy-benzoic acid (gallic acid), pyromucic acid (furan-2-carboxylic acid), 2-methyl-benzoic acid (o-toluic acid), 3,6,9-trioxa-undecanedioic acid, 3-(4-methoxyphenyl)-propionic acid (p-methoxy-hydrocinnamic acid), 3-(3,4-dihydroxyphenyl)-propionic acid, O-acetyl-salicylic acid (aspirin), 3-fluoro-benzoic acid, cyclohexanecarboxylic acid, 5-chloro-2-hydroxy-benzoic acid (5-chloro-salicylic acid), 2,5-dimethyl-benzoic acid (p-xylic acid), 3,4,5-trimethoxy-benzoic acid (trimethylgallic acid), 2,4,6-trimethyl-benzoic acid, 3-phenoxy-benzoic acid, 4-phenyl-butyric acid, 3-trifluoromethyl-benzoic acid, terephthalic acid monomethyl ester, o-hydroxy-phenyl-acetic acid, isophthalic acid, 2,4,6-trihydroxy-benzoic acid, trifluoromethanesulfonic acid, 2-methyl-propionic acid (iso-butyric acid), 2,4-dimethoxy-benzoic acid, 2-thienylacetic acid (thiophene-2-acetic acid), 3,4-dimethoxy-benzoic acid (veratric acid), 2,2-bis(hydroxy-methyl)-propionic acid, 2-fluoro-phenylacetic acid, 2-methyl-butyric acid, hydroxy-acetic acid, 4-chloro-phenylacetic acid, 2-mercaptobenzoic acid (thiosalicylic acid), (+/−)-2-hydroxyphenyl-acetic acid (DL-mandelic acid), 2,4-dihydroxypyrimidine-6-carboxylic acid, toluene-4-sulfonic acid (p-toluene-sulfonic acid), 2-chloro-phenylacetic acid, 2,4-dichloro-benzoic acid, 2,6-dichloro-benzoic acid, 2-mercapto-propionic acid (thiolactic acid), 2-chloro-benzoic acid, methanesulfonic acid, ethanesulfonic acid (ethyl-sulfuric acid), 4-phenoxy-butyric acid, 4-tert-butyl-benzoic acid, 3,4-methylenedioxy-benzoic acid, bis(2-carboxyethyl)-disulfide, pivalic acid (trimethylacetic acid), nicotinic acid N-oxide, acrylic acid, 3-benzoyl-propionic acid (4-oxo-4-phenyl-butyric acid), (1R)-(−)-camphor-10-sulfonic acid hydrate, 2-chloro-4-fluoro-benzoic acid, 3,5-dimethoxy-benzoic acid, 2-sulfobenzoic acid, sulfoacetic acid, 2-chloro-6-fluoro-benzoic acid, 2,4-dihydroxy-benzoic acid, methoxyacetic acid, 2,4,6-trimethyl-benzene-sulfonic acid, tartaric acid, xanthene-9-carboxylic acid, 4-pentenoic acid (allylacetic acid), 5-sulfosalicylic acid, vinylacetic acid, 2-butynedioic acid (acetylenedicarboxylic acid), 2-oxo-propionic acid (pyruvic acid), cyclohexylacetic acid, 2-hydroxyisobutyric acid, nicotinic acid, 6-chloro-nicotinic acid, isonicotinic acid, picolinic acid, pyrazinecarboxylic acid, oxalic acid, propionic acid, pentafluoropropionic acid, butyric acid, heptafluorobutyric acid, valeric acid, citric acid, glyceric acid, acetic acid, chloroacetic acid, dichloroacetic acid, trifluoroacetic acid, fluoroacetic acid, lactic acid, malonic acid, succinic acid, glutaric acid, adipic acid, pimelic acid, suberic acid, azelaic acid, sebacicacid, phthalic acid, terephthalic acid, phosphoric acid, sulfuric acid, hydrochloric acid, hydrobromic acid, hydriodic acid, nitric acid, perchloric acid, acetoacetic acid, cyanoacetic acid, tetrahydrofuran-2-carboxylic acid, propiolic acid, methacrylic acid, crotonic acid and picric acid.

Unless defined otherwise, the general terms used hereinbefore and hereinafter have the meanings given below.

Unless defined otherwise, carbon-containing groups and compounds each contain from 1 up to and including 6, preferably from 1 up to and including 4, especially 1 or 2, carbon atoms.

Halogen—as a group per se and as a structural element of other groups and compounds, such as haloalkyl, haloalkoxy and haloalkylthio—is fluorine, chlorine, bromine or iodine, especially fluorine, chlorine or bromine, more especially fluorine or chlorine.

Alkyl—as a group per se and as a structural element of other groups and compounds, such as haloalkyl, alkoxy and alkylthio—is, in each case giving consideration to the number of carbon atoms contained in the group or compound in question, either straight-chained, i.e. methyl, ethyl, propyl, butyl, pentyl, hexyl, heptyl or octyl, or branched, e.g. isopropyl, isobutyl, sec-butyl, tert-butyl, isopentyl, neopentyl or isohexyl.

Cycloalkyl—as a group per se and as a structural element of other groups and compounds, such as halocycloalkyl, cycloalkoxy and cycloalkylthio—is, in each case giving due consideration to the number of carbon atoms contained in the group or compound in question, cyclopropyl, cyclobutyl, cyclopentyl, cyclohexyl, cycloheptyl or cyclooctyl.

Alkenyl—as a group per se and as a structural element of other groups and compounds—is, giving due consideration to the number of carbon atoms and conjugated or isolated double bonds contained in the group in question, either straight-chained, e.g. vinyl, allyl, 2-butenyl, 3-pentenyl, 1-hexenyl, 1-heptenyl, 1,3-hexadienyl or 1,3-octadienyl, or branched, e.g. isopropenyl, isobutenyl, ispprenyl, tert-pentenyl, isohexenyl, isoheptenyl or isooctenyl. Alkenyl groups having from 3 to 12, especially from 3 to 6, more especially 3 or 4, carbon atoms are preferred.

Alkynyl—as a group per se and as a structural element of other groups and compounds—is, in each case giving due consideration to the number of carbon atoms and conjugated or isolated double bonds contained in the group or compound in question, either straight-chained, e.g. ethynyl, propargyl, 2-butynyl, 3-pentynyl, 1-hexynyl, 1-heptynyl, 3-hexen-1-ynyl or 1,5-heptadien-3-ynyl, or branched, e.g. 3-methylbut-1-ynyl, 4-ethylpent-1-ynyl, 4-methylhex-2-ynyl or 2-methylhept-3-ynyl. Alkynyl groups having from 3 to 12, especially from 3 to 6, more especially 3 or 4, carbon atoms are preferred.

Alkylene and alkenylene are straight-chain or branched bridge members; they are in particular —$CH_2CH_2CH_2$—, —$CH_2CH_2CH_2CH_2$—, —$CH_2CH_2CH_2CH_2CH_2$—, —$CH_2(CH_3)CH_2CH_2$—, —$CH_2C(CH_3)_2CH_2$—, —$CH_2CH=CH$—, —$CH_2CH=CHCH_2$— or —$CH_2CH=CHCH_2CH_2$—.

Halo-substituted carbon-containing groups and compounds, such as alkyl, alkenyl, alkynyl, cycloalkyl, alkoxy or alkylthio substituted by halogen, may be partially halogenated or perhalogenated, it being possible in the case of polyhalogenation for the halogen substituents to be the same or different. Examples of haloalkyl—as a group per se and as a structural element of other groups and compounds, such as haloalkoxy and haloalkylthio—are methyl substituted from one to three times by fluorine, chlorine and/or bromine, such as $CHF_2$ or $CF_3$; ethyl substituted from one to five times by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl substituted from one to seven times by fluorine, chlorine and/or bromine, such as $CH_2CHBrCH_2Br$, $CF_2CHFCF_3$, $CH_2CF_2CF_3$ or $CH(CF_3)_2$; butyl or an isomer thereof substituted from one to nine times by fluorine, chorine and/or bromine, such as $CF(CF_3)CHFCF_3$ or $CH_2(CF_2)_2CF_3$; pentyl or an isomer thereof substituted from one to eleven times by fluorine, chlorine and/or bromine, such as $CF(CF_3)(CHF)_2CF_3$ or $CH_2(CF_2)_3CF_3$; and hexyl or an isomer thereof substituted from one to thirteen times by fluorine, chlorine and/or bromine, such as $(CH_2)_4CHBrCH_2Br$, $CF_2(CHF)_4CF_3$, $CH_2(CF_2)_4CF_3$ or $C(CF_3)_2(CHF)_2CF_3$.

Aryl is especially phenyl, naphthyl, anthracenyl or perylenyl, preferably phenyl.

Heterocyclyl is especially pyridyl, pyrimidyl, s-triazinyl, 1,2,4-triazinyl, thienyl, furyl, tetrahydrofuranyl, pyranyl, tetrahydropyranyl, pyrrolyl, pyrazolyl, imidazolyl, thiazolyl, triazolyl, oxazolyl, thiadiazolyl, oxadiazolyl, benzothienyl, quinolinyl, quinoxalinyl, benzofuranyl, benzimidazolyl, benzopyrrolyl, benzothiazolyl, indolyl, coumarinyl or indazolyl, which are preferably bonded via a carbon atom; preference is given to thienyl, thiazolyl, benzofuranyl, benzothiazolyl, furyl, tetrahydropyranyl and indolyl; especially pyridyl or thiazolyl.

Within the scope of the present invention, preference is given to (2) compounds according to group (1) of formula (I) wherein $R_1$ is isopropyl or sec-butyl, preferably wherein a mixture of the isopropyl and the sec-butyl derivative is present;

(3) compounds according to group (1) or (2) of formula (I) wherein $R_2$ is H;

(4) compounds according to group (1) or (2) of formula (I) wherein $R_2$ is unsubstituted or substituted, especially unsubstituted, $C_1$-$C_8$alkyl, most especially methyl;

(5) compounds according to group (1) or (2) of formula (I) wherein $R_2$ is ethyl;

(6) compounds according to group (1) or (2) of formula (I) wherein $R_2$ is n-propyl;

(7) compounds according to any one of groups (1) to (6) of formula (I) wherein $R_3$ is unsubstituted or substituted, especially unsubstituted, $C_1$-$C_{12}$alkyl;

(8) compounds according to any one of groups (1) to (6) of formula (I) wherein $R_3$ is hydrogen;

(9) compounds according to any one of groups (1) to (7) of formula (I) wherein $R_3$ is methyl;

(10) compounds according to any one of groups (1) to (7) of formula (I) wherein $R_3$ is ethyl;

(11) compounds according to any one of groups (1) to (7) of formula (I) wherein $R_3$ is n-propyl;

(12) compounds according to any one of groups (1) to (7) of formula (I) wherein $R_3$ is iso-propyl;

(13) compounds according to any one of groups (1) to (7) of formula (I) wherein $R_3$ is n-butyl, sec-butyl, iso-butyl or tert-butyl;

(14) compounds according to any one of groups (1), (2), (4) and (7) to (13) of formula (I) wherein $R_2$ is substituted $C_1$-$C_4$alkyl and the substituents are selected from the group consisting of OH, halogen, $C_3$-$C_8$cycloalkyl; $C_3$-$C_8$cycloalkenyl that is unsubstituted or substituted by from one to three methyl groups; $C_1$-$C_{12}$alkoxy, $C_2$-$C_4$alkenyl, $C_2$-$C_8$alkynyl, —C(=O)—$R_5$, —NHC(=O)$R_6$, —P(=O)(O$C_1$-$C_6$alkyl)$_2$; and phenyl, naphthyl, anthracenyl, phenanthrenyl, fluorenyl, perylenyl and heterocyclyl which are unsubstituted or, depending upon the possibilities of substitution at the ring, mono- to penta-substituted;

especially wherein the substituents of $R_2$ are selected from the group consisting of halogen, $C_3$-$C_8$cycloalkyl, $C_2$-$C_8$alkynyl, —C(=O)—$R_5$, —NHC(=O)$R_6$, —P(=O)(O$C_1$-$C_6$alkyl)$_2$; and phenyl, naphthyl, anthracenyl, pyridyl, thiazolyl, imidazolyl, furyl, quinolinyl and pyrazolyl which are unsubstituted or, depending upon the possibilities of substitution at the ring, mono- to tri-substituted;

(15) compounds according to any one of groups (1), (2) and (7) to (14) of formula (I) wherein $R_2$ is unsubstituted or substituted, especially unsubstituted, $C_1$-$C_6$alkoxy-$C_1$-$C_6$alkyl;

(16) compounds according to any one of groups (1) to (6), (14) and (15) of formula (I) wherein $R_3$ is benzyl that carries on the aromatic moiety from one to three substituents that are selected from the group consisting of OH, halogen, CN, NO$_2$, $C_1$-$C_2$alkyl, dimethylamino-$C_1$-$C_4$alkoxy, $C_3$-$C_6$cycloalkyl, $C_1$-$C_2$haloalkyl, $C_1$-$C_2$alkoxy, $C_1$-$C_2$haloalkoxy, phenoxy, phenyl-$C_1$-$C_6$alkyl, phenyl-$C_1$-$C_4$alkenyl; phenoxy that is unsubstituted or substituted by chlorine or methoxy; benzyloxy that is unsubstituted or substituted by chlorine, methoxy or trifluoromethyl; methylenedioxy, —C(=O)—$R_5$, —O—C(=O)$R_6$ and NHC(=O)$R_6$;

$R_5$ is H, OH, NH$_2$, NH($C_1$-$C_2$alkyl), N($C_1$-$C_2$alkyl)$_2$, —O—$C_1$-$C_2$alkyl-C(=O)—$R_7$, NHC$_1$-$C_2$alkyl-C(=O)—$R_7$, $C_1$-$C_6$alkyl, $C_1$-$C_2$alkoxy, $C_1$-$C_2$alkoxy-$C_1$-$C_2$alkoxy, $C_2$-$C_4$alkenyloxy, $C_2$-$C_4$alkynyloxy; phenyl, phenoxy, benzyloxy, NH-phenyl, NH—$C_1$-$C_6$alkyl-C(=O)—$R_7$; or phenyl, phenoxy, benzyloxy, NH-phenyl that are substituted by halogen, nitro, methoxy, trifluoromethyl or trifluoromethoxy;

$R_6$ is H, $C_1$-$C_3$alkyl, phenyl or benzyl; and $R_7$ is H, OH, NH$_2$, NH($C_1$-$C_{12}$alkyl), N($C_1$-$C_{12}$alkyl)$_2$, $C_1$-$C_{12}$alkyl, $C_1$-$C_{12}$alkoxy, $C_1$-$C_6$alkoxy-$C_1$-$C_6$alkoxy, $C_2$-$C_8$alkenyloxy, phenyl, phenoxy, benzyloxy or NH-phenyl;

(17) compounds according to any one of groups (1), (2) and (7) to (13) of formula (I) wherein $R_2$ is $C_1$-$C_4$alkyl-C(=O)—$R_5$, especially —CH$_2$—C(=O)—$R_5$; and $R_5$ is H, OH, NH$_2$, NH($C_1$-$C_2$alkyl), N($C_1$-$C_2$alkyl)$_2$, $C_1$-$C_4$alkyl, $C_1$-$C_{12}$alkoxy, $C_2$-$C_4$-alkenyloxy, phenyl, phenoxy, benzyloxy, NH-phenyl, NH—$C_1$-$C_2$alkyl-C(=O)—O—$C_1$-$C_2$alkyl-phenyl, —P(=O)(O$C_1$-$C_6$alkyl)$_2$; or phenyl, phenoxy, benzyloxy or NH-phenyl that are substituted by chlorine, fluorine, methoxy, trifluoromethyl or trifluoromethoxy;

most especially wherein $R_5$ is $C_1$-$C_{12}$alkoxy;

(18) compounds according to any one of groups (1), (2) and (7) to (13) of formula (I) wherein $R_2$ is —CH$_2$-heterocyclyl and heterocyclyl is pyridyl, furyl, tetrahydrofuranyl, pyranyl, tetrahydropyranyl, pyrazolyl, imidazolyl, thiazolyl, benzothienyl, quinolinyl, quinoxalinyl, benzofuranyl, benzimidazolyl, benzopyrrolyl, benzothiazolyl, indolyl, coumarinyl or indazolyl, the mentioned radicals being unsubstituted or mono- or di-substituted by substituents selected independently of one another from halogen, trifluoromethyl, trifluoromethoxy and nitro; especially preferably pyridyl, furyl, pyrazolyl, imidazolyl, thiazolyl, benzimidazolyl, benzopyrrolyl, benzothiazolyl or indolyl each of which is unsubstituted or mono- or di-substituted by substituents selected independently of one another from halogen, trifluoromethyl, trifluoromethoxy and nitro; especially pyridyl or thiazolyl each of which is unsubstituted or mono- or di-substituted by substituents selected independently of one another from halogen, trifluoromethyl, trifluoromethoxy and nitro, especially mono-substituted by chlorine;

(19) compounds according to any one of groups (1) to (6) of formula (I) wherein $R_3$ is $C_2$-$C_{10}$alkenyl, especially $C_2$-$C_4$alkenyl, that is unsubstituted or mono- or di-substituted, especially mono-substituted, by $C_2$-$C_4$alkynyl, —C(=O)—$C_1$-$C_4$alkoxy, —C(=O)—O-benzyl, phenyl or by halogen; especially wherein $R_3$ is —CH$_2$—CH=CH$_2$;

(20) compounds according to any one of groups (1) to (19) of formula (I) wherein Z is —C(=O);

(21) compounds according to any one of groups (1) to (19) of formula (I) wherein Z is —C(=S);

(22) compounds according to any one of groups (1) to (21) of formula (I) wherein X is a bond;

(23) compounds according to any one of groups (1) to (21) of formula (I) wherein X is O;

(24) compounds according to any one of groups (1) to (21) of formula (I) wherein X is NR$_4$ especially NH;

(25) compounds according to any one of groups (1) to (21) of formula (I) wherein X is S;

(26) compounds according to any one of groups (1) to (25) of formula (I) wherein the bond between carbon atoms 22 and 23 is a single bond;

(27) compounds according to any one of groups (1) to (25) of formula (I) wherein the bond between carbon atoms 22 and 23 is double bond;

(28) compounds according to any one of groups (1) or (3) to (27) of the formula (I) in which R, is cyclohexyl;

(29) compounds according to any one of groups (1) or (3) to (27) of the formula (I) in which $R_1$ is 1-methyl-butyl;

(30) compounds according to any one of groups (1), (2) and (26) to (29) of the formula (I) in which $R_2$ is $C_1$-$C_6$alkoxy-$C_1$-$C_6$alkyl.

(31) compounds according to any one of groups (1), (2) and (26) to (29) of the formula (I) in which the group $R_2$—X-Z is —C(=O)H.

(32) compounds according to any one of groups (1), (2) and (26) to (29) of the formula (I) in which group —NR$_3$-Z-X—$R_2$ is —N(CH$_3$)C(=O)CH$_3$;

(33) special preference is given within the scope of the invention to the compounds of formula (I) listed in the Tables, and, where applicable, their E/Z isomers and mixtures of E/Z isomers.

The intermediates of the following formulae

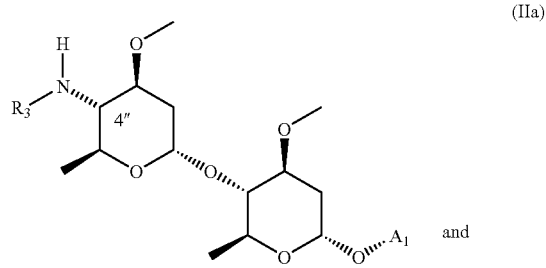

(IIa)

and

-continued

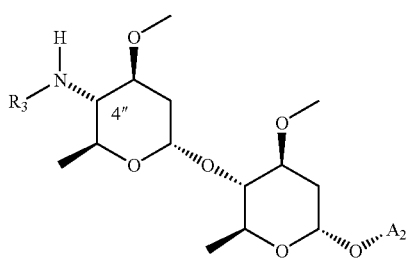

(IIb)

which are used for the preparation of the compounds of formula (I) and wherein $R_3$ is as defined above for formula (I), and $A_1$ and $A_2$ are groups of the formula

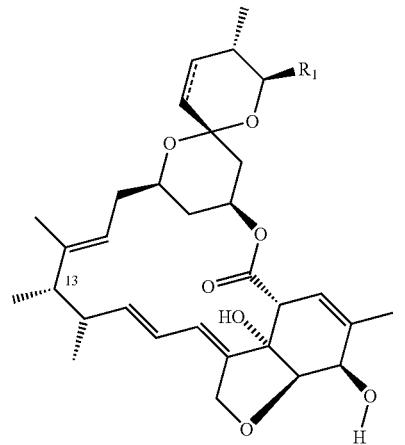

A1 and of the formula

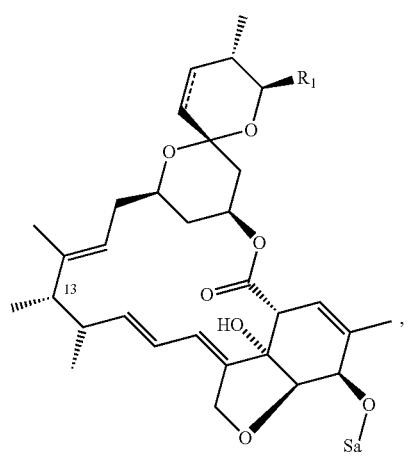

A2 respectively, wherein Sa is a protecting group and $R_1$ is as defined above for formula (I) and the bond between carbon atoms 22 and 23 is a single or a double bond, and wherein the said elements A1 and A2 or connected to the remainder of the structure via carbon atom 13, can be obtained, for example, by (A) reacting a compound of formula

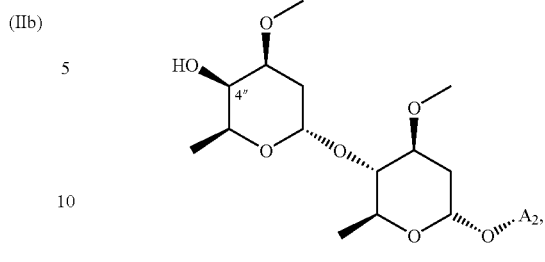

(IIIb)

wherein $A_2$ is as defined above for formula (II) and which is known or can be prepared by methods known per se, with a sulfonic acid derivative to form a compound of formula

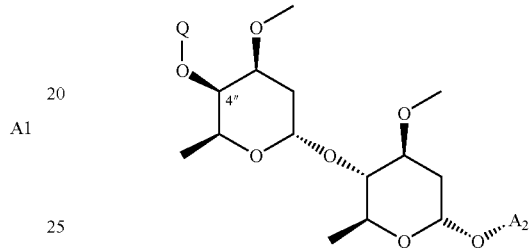

(III)

wherein Q is a sulfonic acid radical and $A_2$ is as defined above for formula (IIb);

(B) reacting the resulting compound of formula (III) with an azide salt, with inversion at the 4"-position, to form a compound of formula

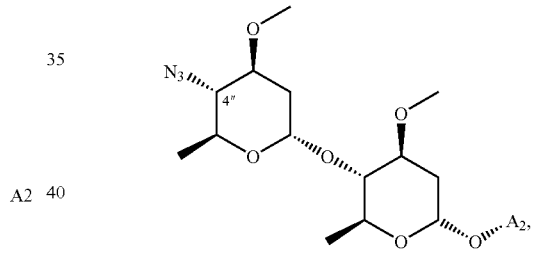

(IVb)

wherein the radical $A_2$ is as defined above; or, where appropriate, (C) for the preparation of a compound of formula (IVb), reacting a compound of formula (IIIb) with an azide in the presence of triphenylphosphine or a trialkylphosphine and an azodicarboxylic acid derivative;

(D) removing the protecting group Sa of the compound of formula (IVb) by reaction with an acid to form a compound of formula

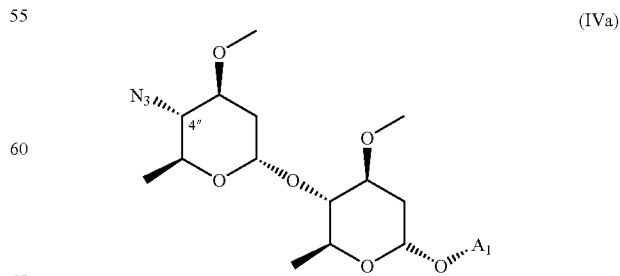

(IVa)

wherein $A_1$ is as defined above;

(E) for the preparation of a compound of formula

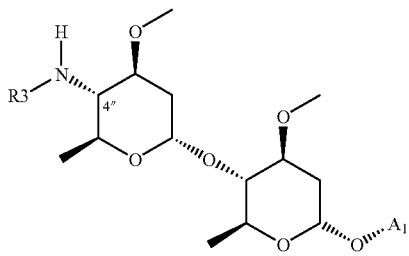

(IIa)

wherein $R_3$ is —$CH_2$—$R_{33}$ and $R_{33}$ is unsubstituted or mono- to penta-substituted $C_1$-$C_{11}$alkyl, unsubstituted or mono- to penta-substituted $C_2$-$C_{11}$alkenyl, or unsubstituted or mono- to penta-substituted $C_2$-$C_{11}$alkynyl, and $A_2$ corresponds to the macrocyclic structure defined for formula (II), reacting a compound of formula (IVb) first (E1) with a phosphine or a phosphite; then
(E2) with an aldehyde of the formula $R_{33}$—CHO; and then
(E3) with a hydride, where appropriate in the presence of a catalytic amount of acid;

(F) removing the protecting group from the resulting compound of formula (IIb) analogously to process step (D); or (G) for the preparation of a compound of formula (IIa) wherein $R_3$ is as defined in process step (E), reacting a compound of formula (IVa) analogously to process steps (E1) to (E3);

(H) for the preparation of a compound of formula (II) wherein $R_3$ is —$CH_3$, reacting a compound of formula (IV) first (H1) with a phosphine; then
(H2) with formaldehyde, preferably in the presence of a molecular sieve; and then
(H3) with a hydride in the presence of a catalytic amount of acid; and further reacting the resulting compound of formula

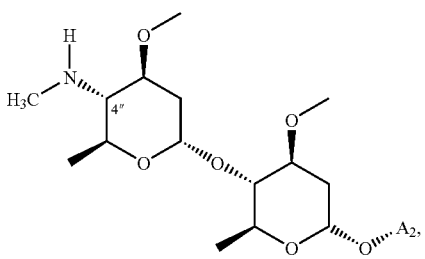

(V)

wherein $A_2$ corresponds to the macrocyclic structure defined for formula (II), analogously to process step (D); or (I) for the preparation of a compound of formula (IIa) wherein $R_3$ is —$CH_3$, reacting a compound of formula (IVa) analogously to process steps (H1) to (H3); or (K) for the preparation of a compound of formula (IIa) or (IIb) wherein $R_3$ is as defined above for formula (I), reacting a compound of formula (IIa) or (IIb) wherein $R_3$ is H with a compound of the formula Hal-$R_{33}$ wherein $R_{33}$ is unsubstituted or mono- to penta-substituted $C_2$-$C_{12}$alkyl or unsubstituted or mono- to penta-substituted $C_2$-$C_{12}$alkenyl and Hal is halogen, preferably iodine or bromine.

Compounds according to the above definition of formulae (IIa) and (IIb) wherein $R_3$ is H and which are used as intermediates for the preparation of the compounds of formula (I) according to the invention can be prepared by (L) either reacting a compound of formula (IVb) analogously to process step (H1) with a phosphine and then with a base; and further reacting the resulting compound of formula (IIb) analogously to process step (D); or reacting a compound of formula (IIa) analogously to process step (H1) with a phosphine and then with a base.

The invention further relates to a process for the preparation of a compound of formula (I) as defined above, wherein (M) a compound of formula (IIa) or (IIb) as defined above is reacted with a compound of the formula $R_2$—X-Z-T, wherein $R_2$, X and Z are as defined for formula (I) and T is a leaving group, and, where appropriate, the resulting compound of formula

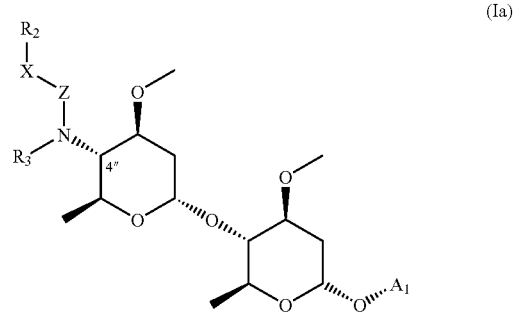

(Ia)

wherein $A_1$, $R_2$ and $R_3$ are as defined above, is further reacted according to process variant (D); or (N) for the preparation of a compound of formula (I) wherein the group $R_2$-Z-X— is $R_2$—NHC(=O)— or $R_2$—NHC(=S)—, and wherein $R_2$ is as defined for formula (I), a compound of formula (IIa) or (IIb) as defined above is reacted with a compound of the formula $R_2$—N=C=O or of the formula $R_2$—N=C=S, wherein $R_2$ is as defined for formula (I), and, where appropriate, the resulting compound of formula (Ia) wherein the group $R_2$-Z-X— is $R_2$—NHC(=O)— or $R_2$—NHC(=S)— is further reacted according to process variant (D).

The remarks made above regarding tautomers of compounds of formula (I) apply analogously to the starting materials mentioned hereinbefore and hereinafter with regard to their tautomers.

The reactions described hereinbefore and hereinafter are carried out in a manner known per se, for example in the absence or, customarily, in the presence of a suitable solvent or diluent or of a mixture thereof, the reactions being carried out, as required, with cooling, at room temperature or with heating, for example in a temperature range of approximately from −80° C. to the boiling temperature of the reaction medium, preferably from approximately 0° C. to approximately +150° C., and, if necessary, in a closed vessel, under pressure, under an inert gas atmosphere and/or under anhydrous conditions. Especially advantageous reaction conditions can be found in the Examples.

The reaction time is not critical; a reaction time of from approximately 0.1 to approximately 72 hours, especially from approximately 0.5 to approximately 24 hours, is preferred.

The product is isolated by customary methods, for example by means of filtration, crystallisation, distillation or chromatography, or any suitable combination of such methods.

The starting materials mentioned hereinbefore and hereinafter that are used for the preparation of the compounds of formula (I) and, where applicable, their tautomers are known or can be prepared by methods known per se, e.g. as indicated below.

Process Variant (A):

Examples of solvents and diluents include: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; or mixtures of the mentioned solvents. Dichloromethane is preferred.

Suitable leaving groups Q in the compounds of formula (III) are especially sulfonic acid radicals; preference is given, for example, to the anions of toluenesulfonic acid, methanesulfonic acid, trifluoromethanesulfonic acid, pentafluoroethanesulfonic acid and nonafluorobutanesulfonic acid.

Suitable protecting groups Sa in the compounds of formulae (II), (III), (IV) and (V) are especially trialkylsilyl groups; preference is given, for example, to trimethylsilyl, triethylsilyl, dimethyl-tert-butylsilyl, dimethyl-isopropylsilyl, dimethyl-1,1,2-trimethylpropylsilyl, diethyl-isopropylsilyl, dimethyl-tert-hexylsilyl, but also phenyl-tert-alkylsilyl groups, such as diphenyl-tert-butylsilyl; or allyloxycarbonyl.

The reactions are advantageously carried out in a temperature range of from approximately −70° C. to +10° C., preferably at from −35° C. to 0° C.

Especially preferred conditions for the reaction are described in Example P.1.

Process Variant (B):

Examples of solvents and diluents include: nitriles, such as acetonitrile; dimethyl sulfoxide; and alcohols, such as, for example, ethanol or methanol; amides, such as dimethylformamide or dimethylacetamide, are especially suitable.

Suitable azide salts are especially $NaN_3$ and $Zn(N_3)_2$; especially $NaN_3$.

The reactions are advantageously carried out in a temperature range of from −10° C. to +10° C.

Especially preferred conditions for the reaction are to be found, for example, in Example P.1.

Process Variant (C):

Examples of solvents and diluents are the same as those mentioned under Process variant (A). In addition, amides, for example, such as dimethylformamide or hexamethylphosphorus triamide, are also suitable.

Suitable azodicarboxylic acid derivatives are especially azodicarboxylic acid esters, for example the dibenzyl, diethyl, dibutyl, diisopropyl or di-tert-butyl ester or the di-(2,2,2-trichloroethyl) ester; or azodicarboxylic acid amides, such as, for example, N,N,N,N-azodicarboxylic acid tetramethylamide or azodicarboxylic acid dimorpholide.

Suitable azide donors are especially $(PhO)_2PN_3$, $Zn(N_3)_2$, pyridine or $HN_3$.

Suitable phosphines are especially trialkyl- and triarylphosphines, such as, for example, trimethylphosphine, triethylphosphine and tri-n-butylphosphine, and triphenylphosphine.

The reactions are advantageously carried out in a temperature range of from −20° C. to 150° C.

Process Variant (D):

Examples of solvents and diluents are the same as those mentioned under Process variant (A). In addition, nitriles, such as acetonitrile; dimethyl sulfoxide; and alcohols, such as, for example, ethanol or methanol; and water are suitable.

The reactions are advantageously carried out in a temperature range of from −10° C. to +25° C.

Suitable acids for the removal of the protecting group are, for example, HF in pyridine, $Zn(BF_4)_2 \cdot H_2O$ or methanesulfonic acid.

Process Variants (E, L):

Examples of solvents and diluents are the same as those mentioned under Process variant (A). In addition, nitriles, such as acetonitrile; and esters of carboxylic acids, such as, for example, ethyl acetate, are suitable.

The reactions are advantageously carried out in a temperature range of from 0° C. to +100° C.

Suitable phosphines are inter alia the same as those mentioned under Process variant (C). Suitable phosphites are, for example, trimethyl phosphite, triethyl phosphite, tri-n-butyl phosphite and tri-tert-butyl phosphite.

Suitable hydrides are, especially, complex hydrides, especially sodium borohydride and sodium cyanoborohydride.

Suitable acids are, especially, weak carboxylic acids, such as acetic acid, propionic acid or pivalic acid; especially pivalic acid. The acids are used especially in catalytic amounts; especially in amounts below 10 mol %, more especially below 5 mol %, most especially below 2 mol %.

Especially preferred conditions for this process variant are described, for example, in Example P.3.

Process Variant (F):

The same process conditions as those described in variant (D) apply. The reaction is preferably carried out in the presence of methanesulfonic acid in methanol at 0° C.

Process Variant (G):

The same process conditions as those described in variant (E) apply.

Process Variant (H):

The same process conditions as those described in variant (E) apply. The phosphine used is, for example, trimethylphosphine or tributylphosphine, preferably trimethylphosphine.

Process Variant (I):

The same process conditions as those described in variant (H) apply.

Process Variant (K):

The same solvents as those indicated under Process variant (A) are used. In addition, amides, such as dimethylformamide and dimethylacetamide; nitriles, such as acetonitrile; and esters, such as ethyl acetate, are also suitable.

Suitable bases are especially carbonates, such as sodium carbonate, sodium hydrogen carbonate, potassium carbonate, trialkylamines, such as triethylamine, and heterocyclic bases, such as, for example, pyridine.

Process Variant (L):

Suitable solvents and diluents are the same as those mentioned under Process variant (A). In addition, nitrites, such as acetonitrile; and esters of carboxylic acids, such as, for example, ethyl acetate, are suitable.

Suitable phosphines are especially trialkyl- and triarylphosphines, such as, for exam-ple, trimethylphosphine and tri-n-butylphosphine and also triphenylphosphine.

There are used as bases especially sodium hydroxide solution or ammonia, especially in highly dilute form, especially, for example, in a concentration of 0.01 N.

Process Variant (M):

Suitable leaving groups are especially halogens, especially bromine or chlorine.

Suitable solvents are those which are inert under the reaction conditions; these include especially those mentioned under Process variant (A).

The procedure is carried out at temperatures of from 0° C. to the boiling point of the respective solvent.

Suitable bases are especially carbonates, such as sodium carbonate, sodium hydrogen carbonate or potassium carbonate, trialkylamines, such as triethylamine, and heterocyclic bases, such as, for example, pyridine.

Process Variant (N):

Suitable solvents are those which are inert under the reaction conditions; these include especially those mentioned under Process variant (A).

The procedure is carried out at temperatures of from 0° C. to the boiling point of the respective solvent, especially at from 20° C. to 40° C.

The compounds of formula (I) may be in the form of one of the possible isomers or in the form of a mixture thereof, in the form of pure isomers or in the form of an isomeric mixture, i.e. in the form of a diastereomeric mixture; the invention relates both to the pure isomers and to the diastereomeric mixtures and is to be interpreted accordingly hereinabove and hereinbelow, even i stereochemical details are not mentioned specifically in every case.

The diastereomeric mixtures can be resolved into the pure isomers by known methods, for example by recrystallisation from a solvent, by chromatography, for example high pressure liquid chromatography (HPLC) on acetylcellulose, with the aid of suitable microorganisms, by cleavage with specific, immobilised enzymes, or via the formation of inclusion compounds, for example using crown ethers, only one isomer being complexed.

Apart from by separation of corresponding mixtures of isomers, pure diastereoisomers can be obtained according to the invention also by generally known methods of stereoselective synthesis, for example by carrying out the process according to the invention using starting materials having correspondingly suitable stereochemistry.

In each case it is advantageous to isolate or synthesise the biologically more active isomer, where the individual components have different biological activity.

The compounds of formula (I) may also be obtained in the form of their hydrates and/or may include other solvents, for example solvents which may have been used for the crystallisation of compounds in solid form.

The invention relates to all those embodiments of the process according to which a compound obtainable as starting material or intermediate at any stage of the process is used as starting material and all or some of the remaining steps are carried out, or in which a starting material is used in the form of a derivative and/or a salt and/or its diastereomers, or, especially, is formed under the reaction conditions. For instance compounds of formula (I) bearing a functional group in its free or protected form can be used as starting materials for the preparation of further compounds of formula (I). For such manipulations methods known to the person skilled in the art can be applied.

In the processes of the present invention it is preferable to use those starting materials and intermediates which result in the compounds of formula (I) that are especially preferred.

The invention relates especially to the preparation processes described in the Examples.

In the area of pest control, the compounds of formula (I) according to the invention are active ingredients exhibiting valuable preventive and/or curative activity with a very advantageous biocidal spectrum and a very broad spectrum, even at low rates of concentration, while being well tolerated by warm-blooded animals, fish and plants. They are, surprisingly, equally suitable for controlling both plant pests and ecto- and endo-parasites in humans and more especially in productive livestock, domestic animals and pets. They are effective against all or individual development stages of normally sensitive animal pests, but also of resistant animal pests, such as insects and members of the order Acarina, nematodes, cestodes and trematodes, while at the same time protecting useful organisms. The insecticidal or acaricidal activity of the active ingredients according to the invention may manifest itself directly, i.e. in the mortality of the pests, which occurs immediately or only after some time, for example during moulting, or indirectly, for example in reduced oviposition and/or hatching rate, good activity corresponding to a mortality of at least 50 to 60%.

The action of the compounds according to the invention and the compositions comprising them against animal pests can be significantly broadened and adapted to the given circumstances by the addition of other insecticides, acaricides or nematicides. Suitable additives include, for example, representatives of the following classes of active ingredient: organophosphorus compounds, nitrophenols and derivatives, formamidines, ureas, carbamates, pyrethroids, chlorinated hydrocarbons, neonicotinoids and *Bacillus thuringiensis* preparations.

Examples of especially suitable mixing partners include: azamethiphos; chlorfenvinphos; cypermethrin, cypermethrin high-cis; cyromazine; diafenthiuron; diazinon; dichlorvos; dicrotophos; dicyclanil; fenoxycarb; fluazuron; furathiocarb; isazofos; iodfenphos; kinoprene; lufenuron; methacriphos; methidathion; monocrotophos; phosphamidon; profenofos; diofenolan; a compound obtainable from the Bacillus thuringiensis strain GC91 or from strain NCTC11821; pymetrozine; bromopropylate; methoprene; disulfoton; quinalphos; tau-fluvalinate; thiocyclam; thiometon; aldicarb; azinphos-methyl; benfuracarb; bifenthrin; buprofezin; carbofuran; dibutylaminothio; cartap; chlorfluazuron; chlorpyrifos; cyfluthrin; lambda-cyhalothrin; alpha-cypermethrin; zeta-cypermethrin; deltamethrin; diflubenzuron; endosulfan; ethiofencarb; fenitrothion; fenobucarb; fenvalerate; formothion; methiocarb; heptenophos; imidacloprid; isoprocarb; methamidophos; methomyl; mevinphos; parathion; parathion-methyl; phosalone; pirimicarb; propoxur; teflubenzuron; terbufos; triazamate; fenobucarb; tebufenozide; fipronil; beta-cyfluthrin; silafluofen; fenpyroximate; pyridaben; fenazaquin; pyriproxyfen; pyrimidifen; nitenpyram; acetamiprid; avermectin B1 (abamectin); emamectin; emamectinbenzoate; spinosad; a plant extract that is active against insects; a preparation that comprises nematodes and is active against insects; a preparation obtainable from *Bacillus subtilis*; a preparation that comprises fungi and is active against insects; a preparation that comprises viruses and is active against insects; chlorfenapyr; acephate; acrinathrin; alanycarb; alphamethrin; amitraz; AZ 60541; azinphos A; azinphos M; azocyclotin; bendiocarb; bensultap; beta-cyfluthrin; BPMC; brofenprox; bromophos A; bufencarb; butocarboxim; butylpyridaben; cadusafos; carbaryl; carbophenothion; chloethocarb; chlorethoxyfos; chlormephos; cisresmethrin; clocythrin; clofentezine; cyanophos; cycloprothrin; cyhexatin; demeton M; demeton S; demeton-S-methyl; dichlofenthion; dicliphos; diethion; dimethoate; dimethylvinphos; dioxathion; edifenphos; esfenvalerate; ethion; ethofenprox; ethoprophos; etrimphos; fenamiphos; fenbutatin oxide; fenothiocarb; fenpropathrin; fenpyrad; fenthion; fluazinam; flucycloxuron; flucythrinate; flufenoxuron; flufenprox; fonophos; fosthiazate; fubfenprox; HCH; hexaflumuron; hexythiazox; IKI-220; iprobenfos; isofenphos; isoxathion; ivermectin; malathion; mecarbam; mesulfenphos; metaldehyde; metolcarb; milbemectin; moxidectin; naled; NC 184; omethoate; oxamyl; oxydemethon M; oxydeprofos; permethrin; phenthoate; phorate; phosmet; phoxim; pirimiphos M; pirimiphos E; promecarb; propaphos; prothiofos; prothoate; pyrachlophos; pyradaphenthion; pyresmethrin; pyrethrum; tebufenozide; salithion; sebufos; sulfotep; suiprofos; tebufenpyrad; tebupirimphos; tefluthrin; temephos; terbam; tetrachlorvinphos; thiacloprid; thiafenox; thiodicarb; thiofanox; thionazin; thuringiensin; tralomethrin; triarthene; triazophos; triazuron; trichlorfon; triflumuron; trimethacarb; vamidothion; xylylcarb; YI 5301/5302; zetamethrin; DPX-MP062—indoxacarb; methoxyfenozide; bifenazate; XMC (3,5-xylyl methylcarbamate); or the fungus pathogen Metarhizium anisopliae; most especially fipronil, thiamethoxam, or lambda-cyhalothrin.

The said animal pests include, for example, those mentioned in European Patent Application EP-A-736 252, page 5, line 55, to page 6, line 55. The pests mentioned therein are therefore included by reference in the subject matter of the present invention.

It is also possible to control pests of the class Nematoda using the compounds according to the invention. Such pests include, for example, root knot nematodes, cyst-forming nematodes and also stem and leaf nematodes;

especially of *Heterodera* spp., e.g. *Heterodera schachtii*, *Heterodora avenae* and *Heterodora trifolii*; *Globodera* spp., e.g. *Globodera rostochiensis*; *Meloidogyne* spp., e.g. *Meloidogyne incognita* and *Meloidogyne javanica*; *Radopholus* spp., e.g. *Radopholus similis*; *Pratylenchus*, e.g. *Pratylenchus neglectans* and *Pratylenchus penetrans*; *Tylenchulus*, e.g. *Tylenchulus semipenetrans*; *Longidorus*, *Trichodorus*, *Xiphinema*, *Ditylenchus*, *Apheenchoides* and *Anguina*; especially *Meloidogyne*, e.g. *Meloidogyne incognita*, and *Heterodera*, e.g. *Heterodera glycines*.

An especially important aspect of the present invention is the use of the compounds of formula (I) according to the invention in the protection of plants against parasitic feeding pests.

The compounds according to the invention can be used to control, i.e. to inhibit or destroy, pests of the mentioned type occurring on plants, especially on useful plants and ornamentals in agriculture, in horticulture and in forestry, or on parts of such plants, such as the fruits, blossoms, leaves, stems, tubers or roots, while in some cases plant parts that grow later are still protected against those pests.

Target crops include especially cereals, such as wheat, barley, rye, oats, rice, maize and sorghum; beet, such as sugar beet and fodder beet; fruit, e.g. pomes, stone fruit and soft fruit, such as apples, pears, plums, peaches, almonds, cherries and berries, e.g. strawberries, raspberries and blackberries; leguminous plants, such as beans, lentils, peas and soybeans; oil plants, such as rape, mustard, poppy, olives, sunflowers, coconut, castor oil, cocoa and groundnuts; cucurbitaceae, such as marrows, cucumbers and melons; fibre plants, such as cotton, flax, hemp and jute; citrus fruits, such as oranges, lemons, grapefruit and mandarins; vegetables, such as spinach, lettuce, asparagus, brassicas, carrots, onions, tomatoes, potatoes and paprika; lauraceae, such as avocado, cinnamon and camphor; and tobacco, nuts, coffee, aubergines, sugar cane, tea, pepper, vines, hops, bananas, natural rubber plants and ornamentals.

Further areas of use of the compounds according to the invention are the protection of stored goods and storerooms and the protection of raw materials, and also in the hygiene sector, especially the protection of domestic animals and productive livestock against pests of the mentioned type, more especially the protection of domestic animals, especially cats and dogs, from infestation by fleas, ticks and nematodes.

The invention therefore relates also to pesticidal compositions, such as emulsifiable concentrates, suspension concentrates, directly sprayable or dilutable solutions, spreadable pastes, dilute emulsions, wettable powders, soluble powders, dispersible powders, wettable powders, dusts, granules and encapsulations of polymer substances, that comprise at least one of the compounds according to the invention, the choice of formulation being made in accordance with the intended objectives and the prevailing circumstances.

The active ingredient is used in those compositions in pure form, a solid active ingredient, for example, in a specific particle size, or preferably together with at least one of the adjuvants customary in formulation technology, such as extenders, e.g. solvents or solid carriers, or surface-active compounds (surfactants). In the area of parasite control in humans, domestic animals, productive livestock and pets it will be self-evident that only physiologically tolerable additives are used.

As formulation adjuvants there are used, for example, solid carriers, solvents, stabilisers, "slow release" adjuvants, colourings and optionally surface-active substances (surfactants). Suitable carriers and adjuvants include all substances customarily used. As adjuvants, such as solvents, solid carriers, surface-active compounds, non-ionic surfactants, cationic surfactants, anionic surfactants and further adjuvants in the compositions used according to the invention, there come into consideration, for example, those described in EP-A-736 252, page 7, line 51 to page 8, line 39.

The compositions for use in crop protection and in humans, domestic animals and productive livestock generally comprise from 0.1 to 99%, especially from 0.1 to 95%, of active ingredient and from 1 to 99.9%, especially from 5 to 99.9%, of at least one solid or liquid adjuvant, the composition generally including from 0 to 25%, especially from 0.1 to 20%, of surfactants (%=% by weight in each case). Whereas commercial products will preferably be formulated as concentrates, the end user will normally employ dilute formulations having considerably lower concentrations of active ingredient.

Preferred crop protection products have especially the following compositions (%=percent by weight):

| Emulsifiable concentrates: | |
| --- | --- |
| active ingredient: | 1 to 90%, preferably 5 to 20% |
| surfactant: | 1 to 30%, preferably 10 to 20% |
| solvent: | 5 to 98%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surfactant: | 1 to 40%, preferably 2 to 30% |
| Wettable powders: | |
| active ingredient: | 0.5 to 90%, preferably 1 to 80% |
| surfactant: | 0.5 to 20%, preferably 1 to 15% |
| solid carrier: | 5 to 99%, preferably 15 to 98% |
| Granules: | |
| active ingredient: | 0.5 to 30%, preferably 3 to 15% |
| solid carrier: | 99.5 to 70%, preferably 97 to 85% |

The compositions according to the invention may also comprise further solid or liquid adjuvants, such as stabilisers, e.g. vegetable oils or epoxidised vegetable oils (e.g. epoxidised coconut oil, rapeseed oil or soybean oil), antifoams, e.g. silicone oil, preservatives, viscosity regulators, binders and/or tackifiers as well as fertilisers or other active ingredients for obtaining special effects, e.g. acaricides, bactericides, fungicides, nematicides, molluscicides or selective herbicides.

The crop protection products according to the invention are prepared in known manner, in the absence of adjuvants, e.g. by grinding, sieving and/or compressing a solid active ingredient or mixture of active ingredients, for example to a certain particle size, and in the presence of at least one adjuvant, for example by intimately mixing and/or grinding the active ingredient or mixture of active ingredients with the adjuvant(s). The invention relates likewise to those processes for the preparation of the compositions according to the invention and to the use of the compounds of formula (I) in the preparation of those compositions.

The invention relates also to the methods of application of the crop protection products, i.e. the methods of controlling pests of the mentioned type, such as spraying, atomising, dusting, coating, dressing, scattering or pouring, which are selected in accordance with the intended objectives and the prevailing circumstances, and to the use of the compositions for controlling pests of the mentioned type. Typical rates of concentration are from 0.1 to 1000 ppm, preferably from 0.1 to 500 ppm, of active ingredient. The rates of application per hectare are generally from 1 to 2000 g of active ingredient per hectare, especially from 10 to 1000 g/ha, preferably from 20 to 600 g/ha.

A preferred method of application in the area of crop protection is application to the foliage of the plants (foliar application), the frequency and the rate of application being dependent upon the risk of infestation by the pest in question. However, the active ingredient can also penetrate the plants through the roots (systemic action) when the locus of the plants is impregnated with a liquid formulation or when the active ingredient is incorporated in solid form into the locus of the plants, for example into the soil, e.g. in granular form (soil application). In the case of paddy rice crops, such granules may be applied in metered amounts to the flooded rice field.

The crop protection products according to the invention are also suitable for protecting plant propagation material, e.g. seed, such as fruits, tubers or grains, or plant cuttings, against animal pests. The propagation material can be treated with the composition before planting: seed, for example, can be dressed before being sown. The active ingredients according to the invention can also be applied to grains (coating), either by impregnating the seeds in a liquid formulation or by coating them with a solid formulation. The composition can also be applied to the planting site when the propagation material is being planted, for example to the seed furrow during sowing. The invention relates also to such methods of treating plant propagation material and to the plant propagation material so treated.

PREPARATION EXAMPLES

In the following Examples, the preparation of avermectin B1 derivatives (mixtures of avermectin B1a and B1b derivative) is described. The B1b derivative generally represents about only from 5 to 10% by weight of the mixtures and, for that reason, usually only the bands of the B1a derivative can be detected in the NMR spectrum.

The abbreviations used in the NMR data information have the following meanings:

s: singlet; MHz: megahertz; brs: broad singlet; t: triplet; m: multiplet; d: doublet; J: coupling constant.

TBDMS in the Examples represents the radical —Si(CH$_3$)$_2$(tert-butyl), R$_1$ a mixture of isopropyl and sec-butyl.

Since the compounds are in most cases in the form of mixtures of the avermectin B1a and B1b derivative, characterisation by means of the customary physical data such as melting point or refractive index is of little use. For that reason, the compounds are characterised by means of NMR spectroscopy following purification by chromatography, or by reference to the retention times determined in analysis by means of HPLC (high-resolution liquid chromatography), as indicated in the above Examples. The term "B1a" in the formulae of the following Examples and Tables refers to the main component, wherein RI is sec-butyl, with a content usually greater than 80%. "B1b" represents the secondary component, wherein R$_1$ is isopropyl. In the case of the compounds for which a retention time is given only in the B1a column, it is not possible to determine the retention time for the B1b component owing to the small proportion of B1b derivative. Allocation of the correct structures of the B1a and B1b components is carried out by mass spectrometry.

The following method is used for the HPLC analysis in Tables unless otherwise stated:

| HPLC gradient conditions | | | |
|---|---|---|---|
| solvent A: | 0.01% trifluoroacetic acid in H$_2$O | | |
| solvent B: | 0.01% trifluoroacetic acid in CH$_3$CN | | |
| Time [min] | A [%] | B [%] | flow rate [µl/min] |
| 0 | 80 | 20 | 500 |
| 0.1 | 50 | 50 | 500 |
| 10 | 5 | 95 | 500 |
| 15 | 0 | 100 | 500 |
| 17 | 0 | 100 | 500 |
| 17.1 | 80 | 20 | 500 |
| 22 | 80 | 20 | 500 |
| column: | YMC-Pack ODS-AQ | | |
| column length: | 125 mm | | |
| column internal diameter: | 2 mm | | |
| temperature: | 40° C. | | |

The YMC-Pack ODS-AQ column used for chromatography of the compounds is produced by the company YMC, Alte Raesfelderstrasse 6, 46514 Schermbeck, Germany.

Example P.1

Preparation of 4"-deoxy-4"-(S)-formylamino-avermectin B₁ of formula

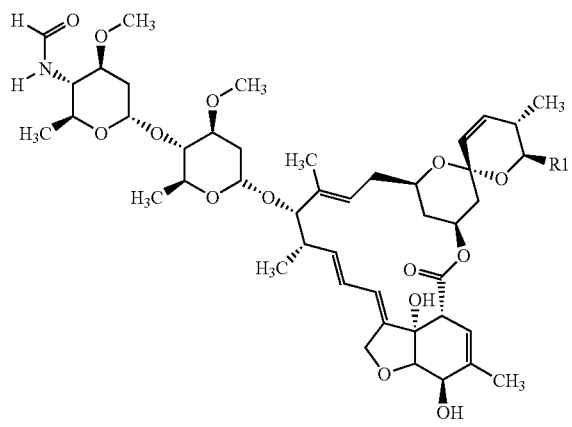

0.05 ml of formic acid-acetic acid anhydride is added to a solution of 100 mg (0.115 mmol) of 4"-deoxy-4"-(S)-amino-avermectin B₁ in 4 ml of THF at room temperature and the mixture is left to stand for 15 hours. For working-up, the mixture is poured onto water and extracted three times with ethyl acetate. The combined organic phases are washed with saturated NaCl solution and dried over Na₂SO₄. The crude product is purified on silica gel in CH₂Cl₂/MeOH (9:1). After drying under a high vacuum, 4"-deoxy-4"-(S)-formylamino-avermectin B₁ is thus obtained as a mixture of rotational isomers that exhibits the following signals in the LC-MS analysis: $t_{RT}$: B$_{1a}$: 7.80 min (88.3%), 900.5 (M+H), B1b: 7.00 min (11.7%), 908.4 (M+Na) (compound 1.001).

Example P.2

Preparation of 4"-deoxy-4"-(S)—N-methyl-acetylamino-avermectin B₁ of formula

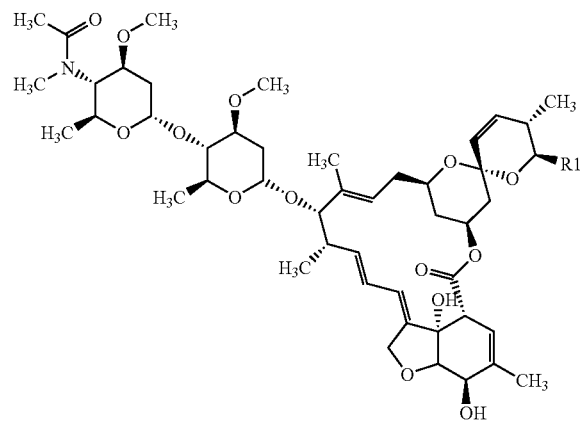

A vigorously stirred two-phase solution consisting of 100 mg of 4"-deoxy-4"-(S)—N-methyl-amino-avermectin B₁ in 5 ml of ethyl acetate and 11.3 ml of saturated NaHCO₃ solution is treated with 115 mg of acetic anhydride for 60 hours at 70° C. under argon. Aqueous working-up with ethyl acetate and purification on silica gel in ethyl acetate/hexane (5:1) yield 4"-deoxy-4"-(S)—N-methyl-acetylamino-avermectin B₁ as a mixture of rotational isomers that exhibits the following signals in the LC-MS analysis: $t_{RT}$: B$_{1a}$: 8.80 min (broad, 100%), 928.7 (M+H), B$_{1b}$:8.16 min (compound 1.002).

Example P.3

Preparation of 4"-deoxy-4"-(S)—N-methyl-methoxycarbonylamino-avermectin B₁ of formula

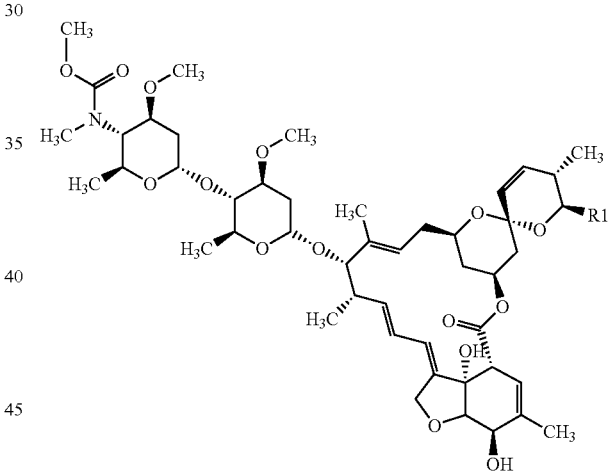

A vigorously stirred two-phase solution consisting of 100 mg of 4"-deoxy-4"-(S)—N-methyl-amino-avermectin B₁ in 5 ml of ethyl acetate and 11.3 ml of saturated NaHCO₃ solution is treated with 0.087 ml of chloroformic acid methyl ester for 3 hours at 65° C. under an argon atmosphere. Aqueous working-up with ethyl acetate followed by purification by chromatography on silica gel in ethyl acetate/hexane (1:1) yields 4"-deoxy-4"-(S)—N-methyl-methoxycarbonylamino-avermectin B₁ as a mixture of rotational isomers that exhibits the following signals in the LC-MS analysis: $t_{RT}$: B$_{1a}$: 10.09 min (86.7%), 966.5 (M+Na), B$_{1b}$: 8.97 min (8.5%): 952.4 (M+Na) (compound 1.003).

Example P.4

Preparation of 4"-deoxy-4"-(S)—N-methyl-methoxyacetylamino-avermectin $B_1$ of formula

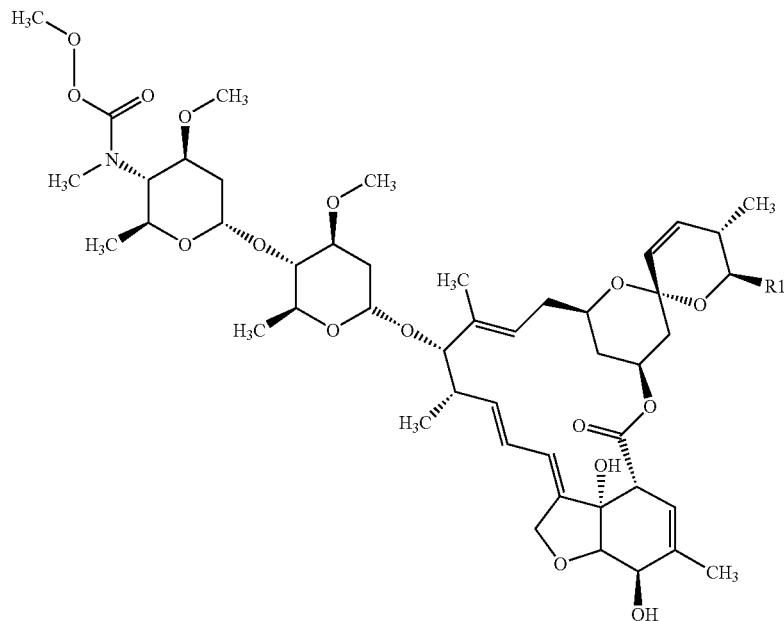

A vigorously stirred two-phase solution consisting of 100 mg of 4"-deoxy-4"-(S)—N-methyl-amino-avermectin $B_1$ in 5 ml of ethyl acetate and 11.3 ml of saturated $NaHCO_3$ solution is treated with 0.103 ml of methoxyacetyl chloride for 12 hours at 70° C. under an argon atmosphere. Aqueous working-up with ethyl acetate followed by purification by chromatography on silica gel in $CH_2Cl_2$/MeOH (95:5) yields 4"-deoxy-4"-(S)—N-methyl-methoxyacetyl-amino-avermectin B1 as a mixture of rotational isomers that exhibits the following signals in the LC-MS analysis: $t_{RT}$: $B_{1a}$: 8.58-8.70 min (92.7%), 980 (M+Na), $B_{1b}$: 8.22 min (7.3%), 966.5 (M+Na) (compound 1.004).

Example P.5

In an analogous manner, the compounds of the following Tables 1A to 1F were prepared. In the tables, the symbol ⁓⁓⁓ indicates the bond by which the radical in question is bonded the remainder of the molecule.

TABLE 1A

Compounds of the formula

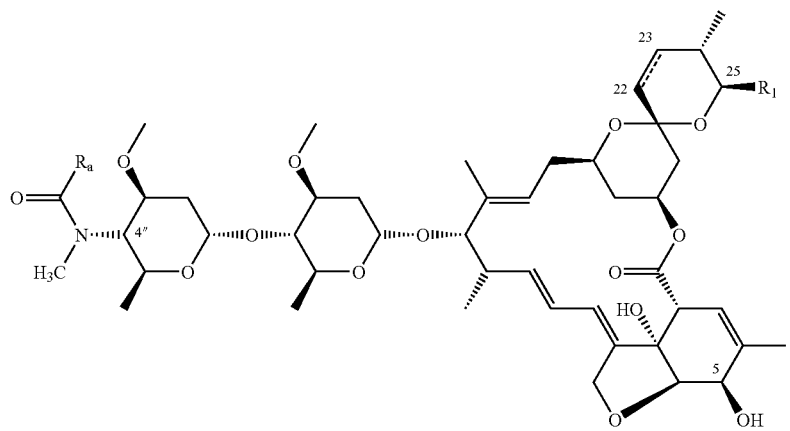

wherein the bond between carbon atoms 22 and 23 is a double bond and $R_1$ is isopropyl or sec-butyl:

| No. | $R_a$ | LC-MS: $t_{RT}$ $B_{1a}$(min) | $B_{1b}$(min) |
|---|---|---|---|
| 1A.005 | H | 8.58 | 8.30 |
| 1A.006 | phenyl | 10.62 | 9.56 |

TABLE 1A-continued

Compounds of the formula

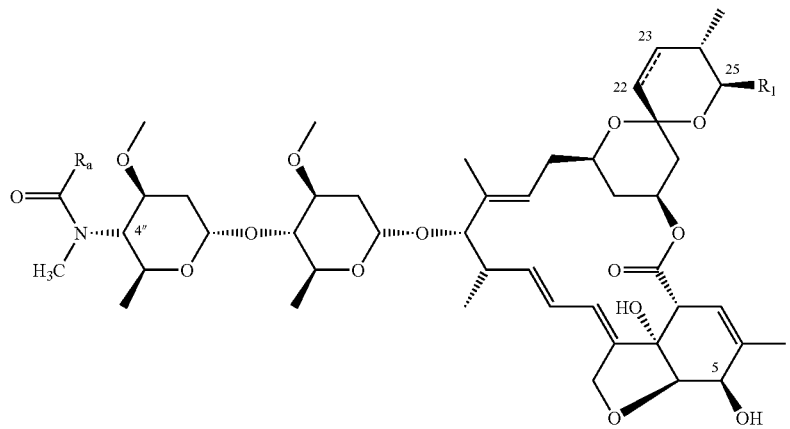

wherein the bond between carbon atoms 22 and 23 is a double bond and $R_1$ is isopropyl or sec-butyl:

| | | LC-MS: $t_{RT}$ | |
|---|---|---|---|
| No. | $R_a$ | $B_{1a}$(min) | $B_{1b}$(min) |
| 1A.007 | H₃C–CH₂–O~ | 10.73 | 9.66 |
| 1A.008 | H₃C–O–C(=O)– | 9.44 | 8.69 |

TABLE 1B

Compounds of the formula

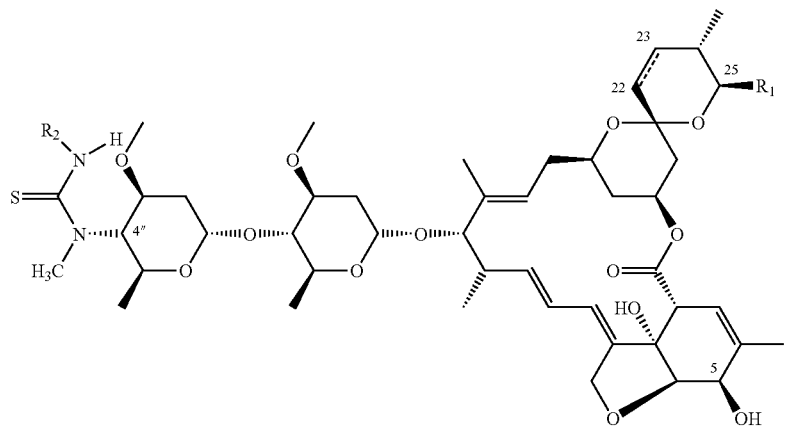

wherein the bond between carbon atoms 22 and 23 is a double bond and $R_1$ is isopropyl or sec-butyl

| | | LC-MS: $t_{RT}$ | |
|---|---|---|---|
| No. | $R_2$ | $B_{1a}$(min) | $B_{1b}$(min) |
| 1B.1 | propyl | 10.2 | |
| 1B.2 | allyl | 9.8 | 9.2 |

TABLE 1B-continued
Compounds of the formula
wherein the bond between carbon atoms 22 and 23 is a double bond and R₁ is isopropyl or sec-butyl
| No. | R₂ | LC-MS: $t_{RT}$ | |
|-----|-----|------|------|
|     |     | $B_{1a}$(min) | $B_{1b}$(min) |
| 1B.3 |  | 10.2 | |
| 1B.4 |  | 9.4 | 8.8 |
| 1B.5 | 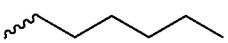 | 10.8 | 10.1 |
| 1B.6 | 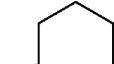 | 11.7 | |
| 1B.7 | 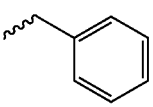 | 11.3 | 10.6 |
| 1B.8 | 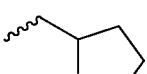 | 10.6 | 9.9 |
| 1B.9 | 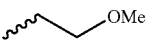 | 9.9 | 9.1 |
| 1B.10 |  | 9.5 | 8.7 |

TABLE 1C
Compounds of the formula
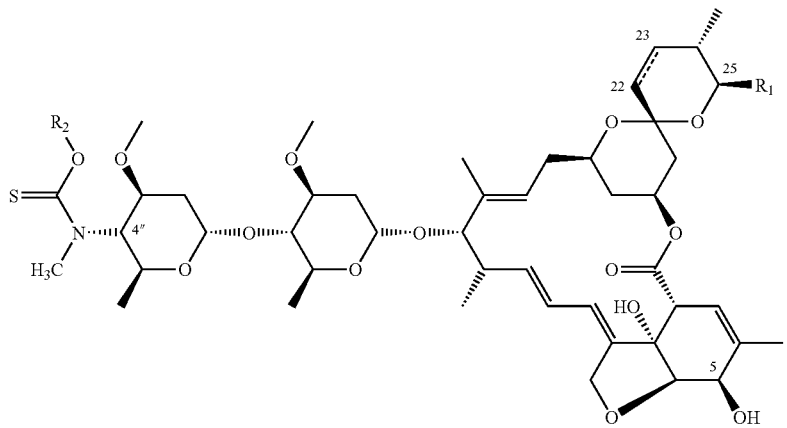
wherein the bond between carbon atoms 22 and 23 is a double bond and $R_1$ is isopropyl or sec-butyl
| No. | $R_2$ | LC-MS: $t_{RT}$ $B_{1a}$(min) | $B_{1b}$(min) |
|---|---|---|---|
| 1C.1 | Ethyl | 11.2 | 10.5 |
TABLE 1D
Compounds of the formula
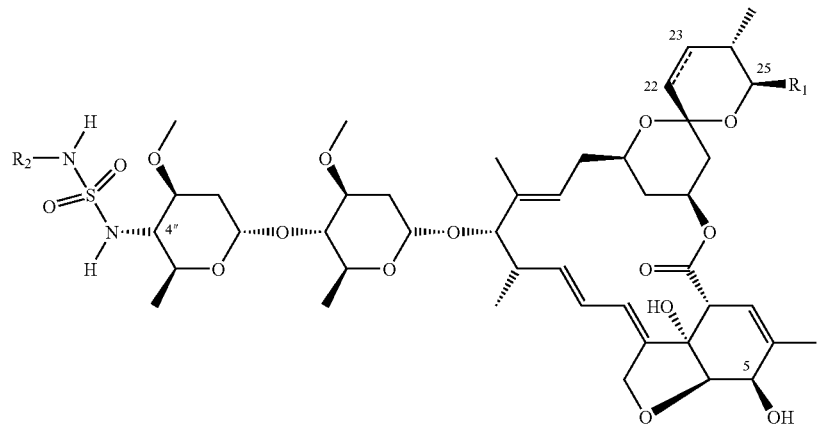
wherein the bond between carbon atoms 22 and 23 is a double bond and $R_1$ is isopropyl or sec-butyl
| No. | $R_2$ | LC-MS: $t_{RT}$ $B_{1a}$(min) | $B_{1b}$(min) |
|---|---|---|---|
| 1D.1 | ![m-CF3-phenyl] | 11.6 | 11.0 |
| 1D.2 | ![p-OMe-phenyl] | 10.7 | — |

TABLE 1D-continued
Compounds of the formula
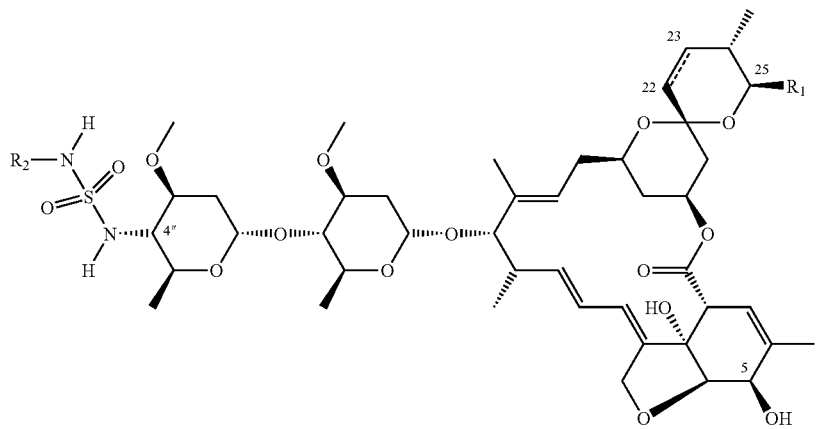
wherein the bond between carbon atoms 22 and 23 is a double bond and R₁ is isopropyl or sec-butyl
| No. | R₂ | LC-MS: $t_{RT}$ | |
|---|---|---|---|
| | | $B_{1a}$(min) | $B_{1b}$(min) |
| 1D.3 | 4-nitrophenyl | 11.0 | |
| 1D.4 | 5-chloro-1,3-dimethyl-1H-pyrazol-4-yl | — | — |
| 1D.5 | 2,4,6-triisopropylphenyl | — | — |
| 1D.6 | 3,5-bis(trifluoromethyl)phenyl | 12.5 | 12.0 |
| 1D.7 | quinolin-8-yl | 11.9 | 11.2 |
| 1D.8 | 2-(trifluoromethyl)phenyl | — | — |

TABLE 1D-continued
Compounds of the formula
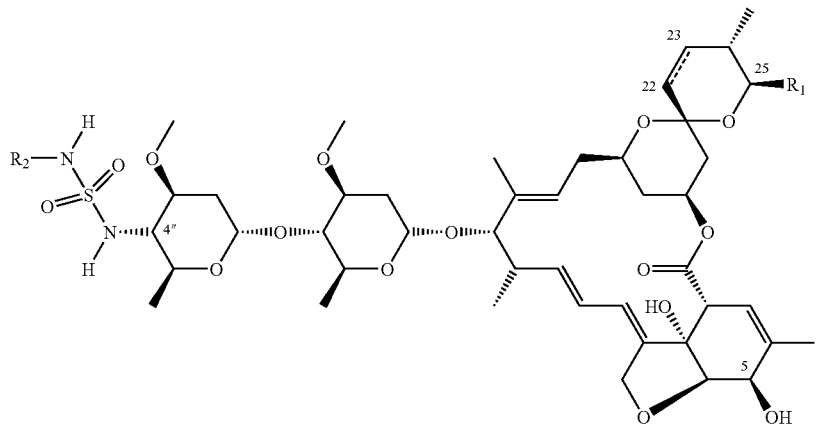
wherein the bond between carbon atoms 22 and 23 is a double bond and $R_1$ is isopropyl or sec-butyl
| No. | $R_2$ | LC-MS: $t_{RT}$ | |
| --- | --- | --- | --- |
| | | $B_{1a}$(min) | $B_{1b}$(min) |
| 1D.9 | 3-nitrophenyl | 11.0 | 10.4 |
| 1D.10 | 2-nitrophenyl | — | — |
| 1D.11 | 2,3-dichlorophenyl (2,3,4-trichloro) | — | — |
| 1D.12 | 2,4,5-trichlorophenyl | — | — |

TABLE 1E

Compounds of the formula

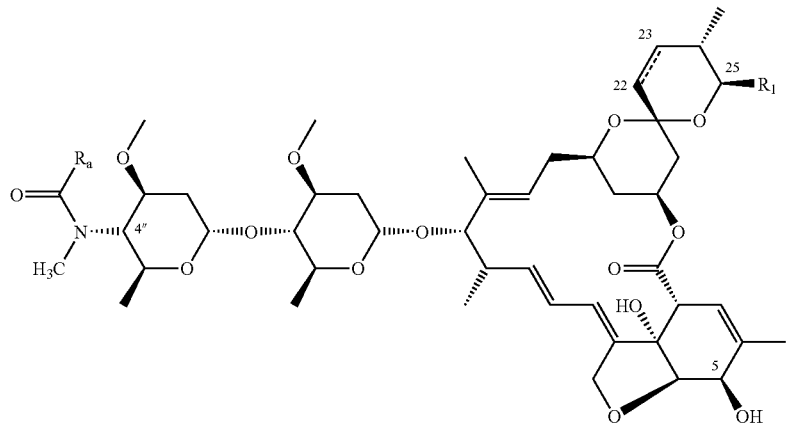

wherein the bond between carbon atoms 22 and 23 is a double bond and $R_1$ is isopropyl or sec-butyl; and wherein the following method is used for the HPLC analysis:

HPLC gradient conditions

Solvent A (%): 45.0 H₂O (containing 0.1% trifluorocetic acid and 10% CH₃CN)
Solvent B (%): 55.0 CH₃CN (containing 0.1% trifluorocetic acid)
Solvent C (%): CH₃OH

| Time [min] | A [%] | B [%] | C [%] | flow rate [ml/min] |
|---|---|---|---|---|
| 0.00 | 45 | 55 | 0 | 3.50 |
| 3.50 | 0 | 90 | 10 | 3.50 |
| 3.80 | 0 | 90 | 10 | 3.50 |
| 4.00 | 45 | 55 | 10 | 3.50 |

Column: YMC CombiScreen ODS-AQ
Column length: 30 mm
Column internal diameter: 4.6 mm
temperature: 40° C.

| No. | $R_a$ | LC-MS: $t_{RT}$ $B_{1a}$(min) | $B_{1b}$(min) |
|---|---|---|---|
| 1E.1 | (3-cyanophenyl) | 2.20 | 2.00 |
| 1E.2 | (O-(CH₂)₄-Cl) | 2.70 | 2.32 |
| 1E.3 | (2-chloropyridin-4-yl) | 2.20 | 2.07 |
| 1E.4 | (5-methylisoxazol-3-yl) | 2.20 | 1.98 |
| 1E.5 | (4-methoxyphenyl) | 2.30 | 1.98 |
| 1E.6 | (3-methoxyphenyl) | 2.40 | 2.03 |

TABLE 1E-continued

| | | | |
|---|---|---|---|
| 1E.7 | 2,4-difluorophenyl | 2.50 | 2.11 |
| 1E.8 | 3,4-difluorophenyl | 2.60 | 2.23 |
| 1E.9 | 4-ethylphenyl | 2.80 | 2.40 |
| 1E.10 | N(Me)CH₂CH₂CN | 1.70 | 1.30 |
| 1E.11 | 5-nitrofuran-2-yl | 2.10 | 2.04 |
| 1E.12 | 4-methyl-1,2,5-thiadiazol-3-yl | 2.20 | 2.03 |
| 1E.13 | 4-methyl-1,2,3-thiadiazol-5-yl | 2.30 | 2.03 |
| 1E.14 | 4-methylphenyl | 2.70 | 2.20 |
| 1E.15 | 2,3-dimethylphenyl | 2.60 | 2.20 |
| 1E.16 | 3-pentyl | 2.50 | 2.00 |
| 1E.17 | C(CN)=N-OMe | 1.70 | 1.70 |
| 1E.18 | C(CN)=N-OEt | 2.60 | 2.20 |
| 1E.19 | 1-chlorocyclopropyl | 2.40 | 2.19 |

TABLE 1E-continued
| | | | |
|---|---|---|---|
| 1E.20 | 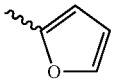 | 2.10 | 1.69 |
| 1E.21 | 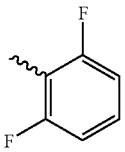 | 2.40 | 1.94 |
| 1E.22 | 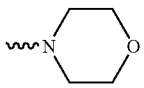 | 1.80 | 1.30 |
| 1E.23 | 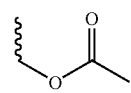 | 1.60 | 1.40 |
| 1E.24 | 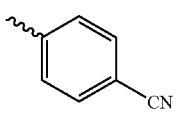 | 2.20 | 1.94 |
| 1E.25 | 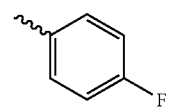 | 2.40 | 2.07 |
| 1E.26 | 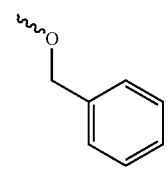 | 2.70 | 2.40 |
| 1E.27 | 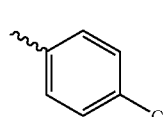 | 1.60 | 1.60 |
| 1E.28 | 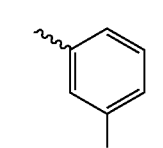 | 2.70 | 2.57 |
| 1E.29 | 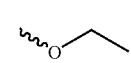 | 2.40 | 1.94 |
| 1E.30 | 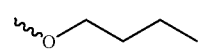 | 2.70 | 2.44 |
| 1E.31 | 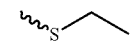 | 2.70 | 2.19 |
| 1E.32 | 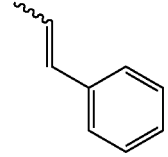 | 2.70 | 2.07 |
| 1E.33 | 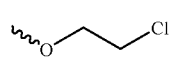 | 2.40 | 2.03 |

TABLE 1E-continued

| | | | |
|---|---|---|---|
| 1E.34 | N-methyl-N-phenyl group | 2.70 | 1.90 |
| 1E.35 | isopropenyl group | 1.4 | 1.4 |
| 1E.36 | thiophen-2-yl group | 2.40 | 1.90 |
| 1E.37 | allyloxy group | 2.50 | 2.03 |
| 1E.38 | but-3-enyloxy group | 1.80 | 1.80 |
| 1E.39 | propoxy group | 2.70 | 2.19 |
| 1E.40 | 2-methylprop-1-enyl group | 2.20 | 1.90 |

TABLE 1F

Compounds of the formula

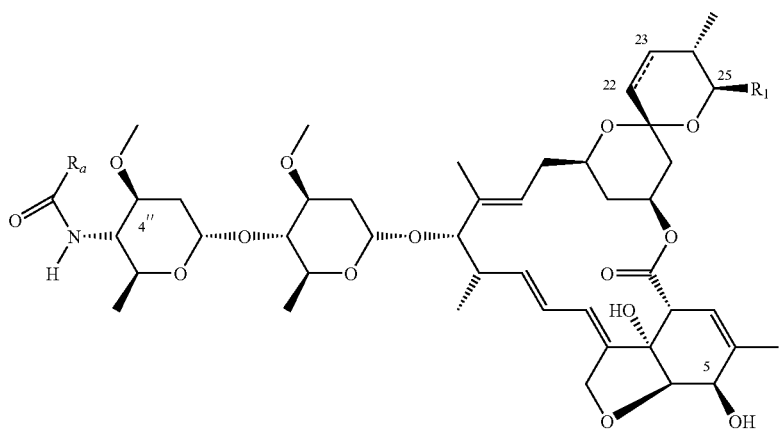

wherein the bond between carbon atoms 22 and 23 is a double bond and $R_1$ is isopropyl or sec-butyl; and wherein the following method is used for the HPLC analysis;

HPLC gradient conditions

| solvent A (%): | 40.0 H$_2$O (containing 0.1% HCO$_2$H) |
| solvent B (%): | 60.0 CH$_3$CN (containing 0.1% HCO$_2$H) |

| Time [min] | A [%] | B [%] | flow rate [ml/min] |
|---|---|---|---|
| 0.00 | 40 | 60 | 3.50 |
| 3.50 | 0 | 100 | 3.50 |
| 3.80 | 0 | 100 | 3.50 |
| 4.00 | 40 | 60 | 3.50 |

| column: | YMC CombiScreen ODS-AQ |
| column length: | 30 mm |
| column internal diameter: | 4.6 mm |
| temperature: | 40° C. |

TABLE 1F-continued

| No. | $R_a$ | LC-MS: $t_{RT}$ | |
|---|---|---|---|
| | | $B_{1a}$ (min) | $B_{1b}$ (min) |
| 1F.1 | 3-CN-phenyl | 1.9 | 1.6 |
| 1F.2 | -O-(CH2)4-Cl | 2.1 | 1.9 |
| 1F.3 | 2-Cl-pyridin-3-yl | 1.5 | 1.3 |
| 1F.4 | 5-methyl-isoxazol-3-yl | 1.8 | 1.5 |
| 1F.5 | 4-methoxyphenyl | 1.8 | 1.5 |
| 1F.6 | syn-propenyl | 1.4 | 1.2 |
| 1F.7 | cyclopentylmethyl | 2.2 | 1.9 |
| 1F.8 | cyclohexyl | 1.9 | 1.7 |
| 1F.9 | 3-methoxyphenyl | 1.9 | 1.6 |
| 1F.10 | cyclobutyl | 1.6 | 1.4 |
| 1F.11 | 2,4-difluorophenyl | 1.9 | 1.7 |
| 1F.12 | 3,4-difluorophenyl | 2.0 | 1.8 |
| 1F.13 | 3,5-difluorophenyl | 2.1 | 1.9 |

TABLE 1F-continued

| | | | |
|---|---|---|---|
| 1F.14 | 4-ethylphenyl | 2.2 | 1.9 |
| 1F.15 | cyclopentyl | 1.7 | 1.5 |
| 1F.16 | N-methyl-N-(cyanomethyl)amino | 1.2 | 1.0 |
| 1F.17 | 5-nitrofuran-2-yl | 1.8 | 1.5 |
| 1F.18 | 4-methyl-1,2,3-thiadiazol-5-yl | 1.9 | 1.6 |
| 1F.19 | isobutyl | 1.9 | 1.7 |
| 1F.20 | 3,5-dimethylisoxazol-4-yl | 1.6 | 1.4 |
| 1F.21 | 2-methylphenyl | 1.9 | 1.7 |
| 1F.22 | 4-methylphenyl | 1.9 | 1.7 |
| 1F.23 | n-propyl | 1.5 | 1.2 |
| 1F.24 | methyl 4-(carboxy)butyl | 1.4 | 1.2 |
| 1F.25 | 2-(acetoxy)prop-2-yl | 1.5 | 1.3 |
| 1F.26 | 2,3-difluorophenyl | 2.0 | 1.7 |
| 1F.27 | cyclopentylmethyl | 1.9 | 1.7 |
| 1F.28 | 2-(methylthio)ethyl | 1.5 | 1.2 |

TABLE 1F-continued

| | | | |
|---|---|---|---|
| 1F.29 | 2,3-dimethylphenyl | 2 | 1.7 |
| 1F.30 | pentan-3-yl | 1.8 | 1.6 |
| 1F.31 | NC-C(=N-OMe)- | 1.9 | 1.7 |
| 1F.32 | NC-C(=N-OEt)- | 2.0 | 1.8 |
| 1F.33 | 1-chlorocyclopropyl | 2.0 | 1.7 |
| 1F.34 | thiophen-2-yl | 1.7 | |
| 1F.35 | -(CH$_2$)$_3$CO$_2$Et | 1.5 | 1.3 |
| 1F.36 | -(CH$_2$)$_3$CO$_2$Me | 1.3 | |
| 1F.37 | 2-fluorophenyl | 1.9 | 1.6 |
| 1F.38 | benzyl | 1.7 | 1.5 |
| 1F.39 | n-pentyl | 2.2 | 1.9 |
| 1F.40 | isopropyl | 1.5 | 1.3 |
| 1F.41 | isobutyl | 1.7 | 1.4 |
| 1F.42 | 4-chlorophenyl | 2.1 | 1.8 |
| 1F.43 | -CH$_2$CH$_2$Cl | 1.5 | 1.3 |

TABLE 1F-continued

| | | | |
|---|---|---|---|
| 1F.44 | 2-methoxyphenyl | 1.9 | 1.7 |
| 1F.45 | 2-chloroethyl | 1.6 | 1.4 |
| 1F.46 | heptyl | 2.4 | 2.1 |
| 1F.47 | 2-furyl | 1.5 | 1.3 |
| 1F.48 | pentyl | 1.9 | 1.7 |
| 1F.49 | 2,6-difluorophenyl | 1.8 | 1.5 |
| 1F.50 | CH₂CH₂OC(O)CH₃ | 1.3 | 1.1 |
| 1F.51 | 3-chlorophenyl | 2.2 | 1.9 |
| 1F.52 | octyl | 2.7 | 2.4 |
| 1F.53 | 4-cyanophenyl | 1.8 | 1.5 |
| 1F.54 | 2,5-difluorophenyl | 2.0 | 1.7 |
| 1F.55 | 4-fluorophenyl | 1.9 | 1.6 |
| 1F.56 | SCH₂CH₃ | 2.1 | 1.8 |
| 1F.57 | N(CH₃)phenyl | 1.7 | 1.5 |
| 1F.58 | 2-thienyl | 1.7 | 1.5 |

TABLE 1F-continued

| | | | |
|---|---|---|---|
| 1F.59 | 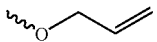 | 1.9 | 1.6 |
| 1F.60 |  | 1.7 | 1.5 |
| 1F.61 | 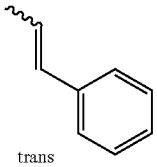 trans | 1.9 | 1.7 |
| 1F.62 | 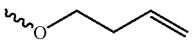 | 2.0 | 1.8 |
| 1F.63 | 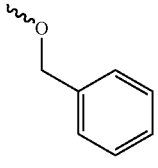 | 2.2 | 1.9 |
| 1F.64 | 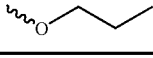 | 2.0 | 1.7 |

Analogously to the above Preparation Examples, the compounds listed in Tables 2 and to 71 can also be prepared. In Table A, the symbol  indicates the bond by which the radical in question is bonded to Z.

TABLE A

Compounds of general formula (I) wherein $R_1$, $R_3$, X and Z are as defined in formula (I) and the bond between carbon atoms 22 and 23 is a double bond

| No. | $R_2$ |
|---|---|
| A.1 | H |
| A.2 | Phenyl |
| A.3 | CH$_3$—O—CH$_2$— |
| A.4 | Methyl |
| A.5 |  |
| A.6 | Ethyl |
| A.7 |  |
| A.8 |  |
| A.9 | Cyclopropyl |
| A.10 | Isopropyl |
| A.11 | n-propyl |
| A.12 | n-butyl |
| A.13 | 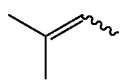 |
| A.14 | Cyclobutyl |

TABLE A-continued

Compounds of general formula (I) wherein $R_1$, $R_3$, X and Z are as defined in formula (I) and the bond between carbon atoms 22 and 23 is a double bond

| A.15 | 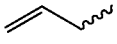 |
|---|---|
| A.16 | Isopropyl |
| A.17 | 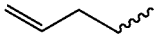 |
| A.18 | 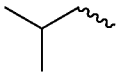 |
| A.19 | Cl 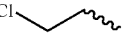 |
| A.20 | Cyclopentyl |
| A.21 |  |
| A.22 | 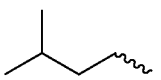 |
| A.23 | 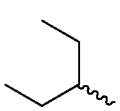 |
| A.24 | n-hexyl |
| A.25 | t-butyl |

TABLE A-continued
Compounds of general formula (I) wherein $R_1$, $R_3$, X and Z are as defined in formula (I) and the bond between carbon atoms 22 and 23 is a double bond
| | | |
|---|---|---|
| A.26 | 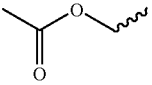 | |
| A.27 | 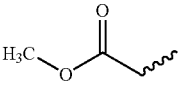 | |
| A.28 | 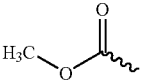 | |
| A.29 | 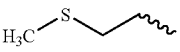 | |
| A.30 | 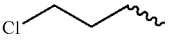 | |
| A.31 | 2-Cl-ethyl | |
| A.32 | Cyclohexyl | |
| A.33 | 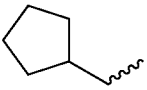 | |
| A.34 | n-heptyl | |
| A.35 | 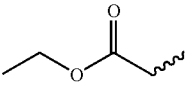 | |
| A.36 | 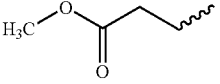 | |
| A.37 | 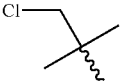 | |
| A.38 | 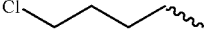 | |
| A.39 | 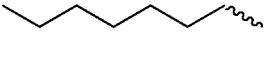 | |
| A.40 | 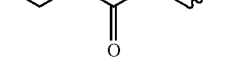 | |
| A.41 | 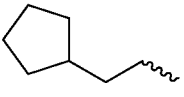 | |
| A.42 |  | |
| A.43 | 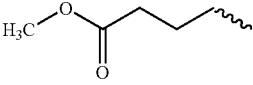 | |
| A.44 | 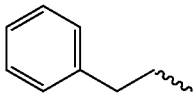 | |
| A.45 | 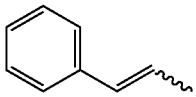 | |
| A.46 | 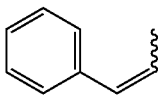 | |
| A.47 | 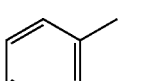 | |
| A.48 | 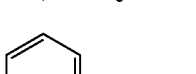 | |
| A.49 | 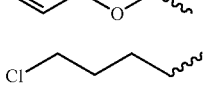 | |
| A.50 | 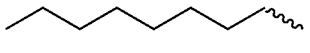 | |
| A.51 | 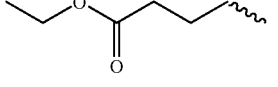 | |
| A.52 | 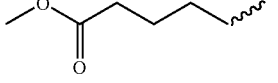 | |
| A.53 | 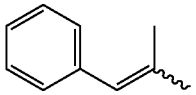 | |
| A.54 | 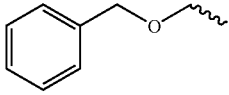 | |
| A.55 | 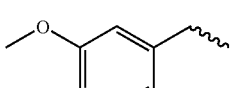 | |
| A.56 | 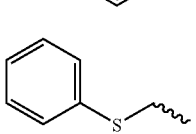 | |
| A.57 |  | |
| A.58 | n-octyl | |
| A.59 | 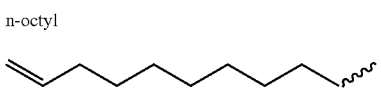 | |

TABLE A-continued
Compounds of general formula (I) wherein $R_1$, $R_3$, X and Z are as defined in formula (I) and the bond between carbon atoms 22 and 23 is a double bond
| | |
|---|---|
| A.60 | 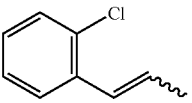 |
| A.61 | 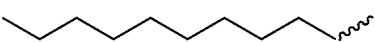 |
| A.62 | 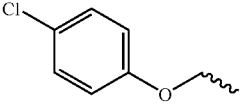 |
| A.63 | 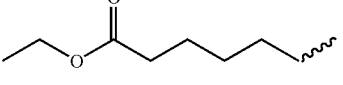 |
| A.64 | 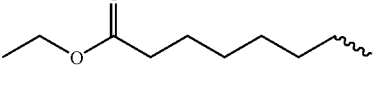 |
| A.65 |  |
| A.66 |  |
| A.67 | 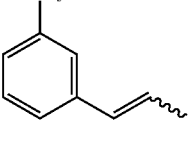 |
| A.68 | 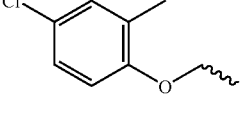 |
| A.69 | 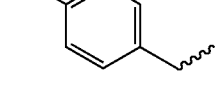 |
| A.70 | 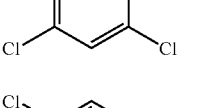 |
| A.71 | 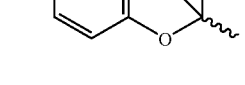 |
| A.72 | 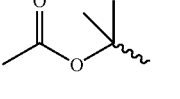 |
TABLE A-continued
Compounds of general formula (I) wherein $R_1$, $R_3$, X and Z are as defined in formula (I) and the bond between carbon atoms 22 and 23 is a double bond
| | |
|---|---|
| A.73 | 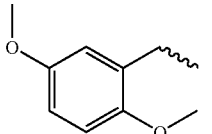 |
| A.74 | 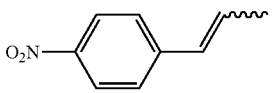 |
| A.75 |  |
| A.76 | 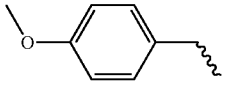 |
| A.77 | 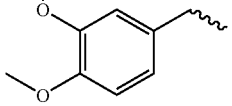 |
| A.78 | 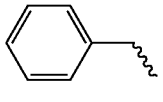 |
| A.79 |  |
| A.80 | 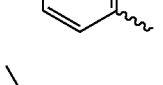 |
| A.81 | 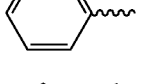 |
| A.82 | 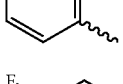 |
| A.83 | 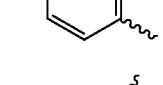 |
| A.84 | 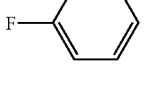 |
| A.85 | 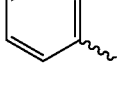 |

TABLE A-continued
Compounds of general formula (I) wherein $R_1$, $R_3$, X and Z are as defined in formula (I) and the bond between carbon atoms 22 and 23 is a double bond
| | | |
|---|---|---|
| A.86 | 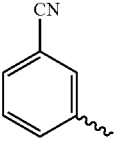 | |
| A.87 |  | |
| A.88 | 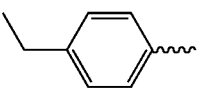 | |
| A.89 | 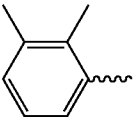 | |
| A.90 | 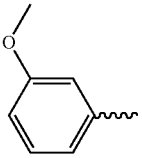 | |
| A.91 | 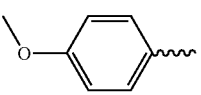 | |
| A.92 | 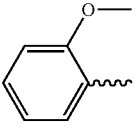 | |
| A.93 | 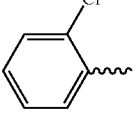 | |
| A.94 | 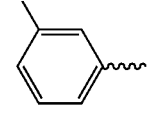 | |
| A.95 | 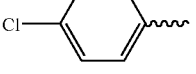 | |
| A.96 | 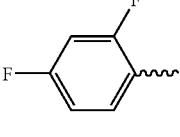 | |
| A.97 | 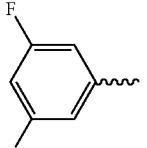 | |
| A.98 | 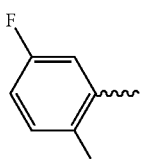 | |
| A.99 | 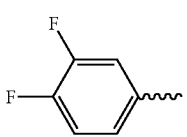 | |
| A.100 | 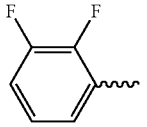 | |
| A.101 | 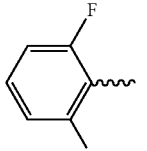 | |
| A.102 | 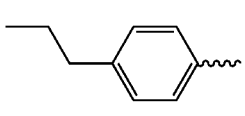 | |
| A.103 | 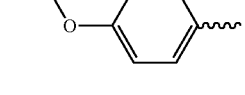 | |
| A.104 | 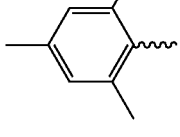 | |
| A.105 | 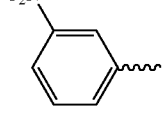 | |
| A.106 | 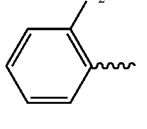 | |

TABLE A-continued
Compounds of general formula (I) wherein $R_1$, $R_3$, X and Z are as defined in formula (I) and the bond between carbon atoms 22 and 23 is a double bond
A.107 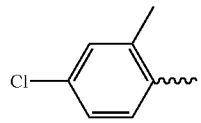
A.108 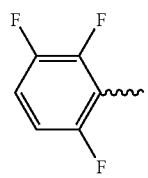
A.109 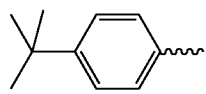
A.110 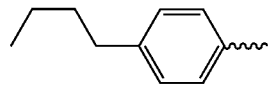
A.111 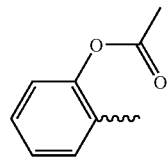
A.112 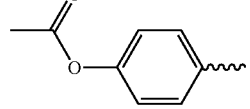
A.113 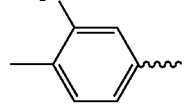
A.114 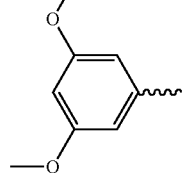
A.115 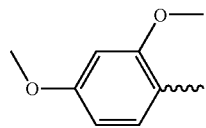
A.116 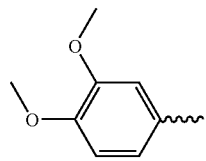
TABLE A-continued
Compounds of general formula (I) wherein $R_1$, $R_3$, X and Z are as defined in formula (I) and the bond between carbon atoms 22 and 23 is a double bond
A.117 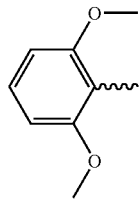
A.118 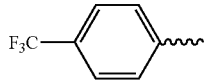
A.119 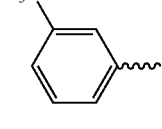
A.120 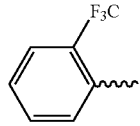
A.121 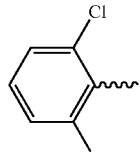
A.122 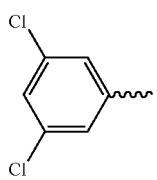
A.123 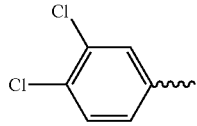
A.124 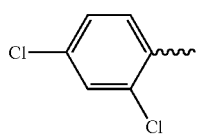
A.125 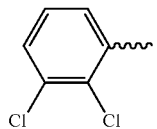
A.126 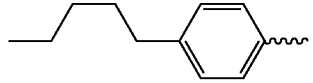

TABLE A-continued
Compounds of general formula (I) wherein $R_1$, $R_3$, X and Z are as defined in formula (I) and the bond between carbon atoms 22 and 23 is a double bond
A.127 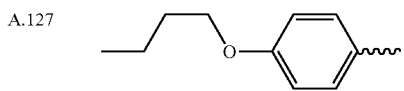
A.128 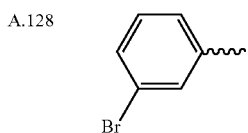
A.129 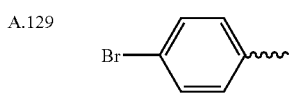
A.130 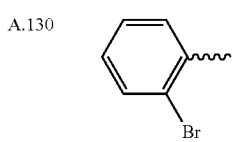
A.131 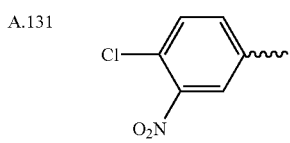
A.132 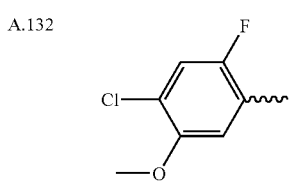
A.133 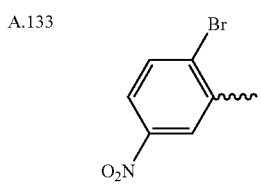
A.134 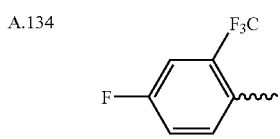
A.135 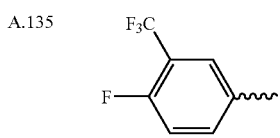
A.136 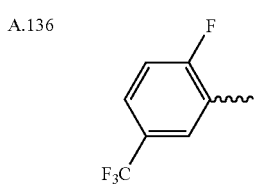
TABLE A-continued
Compounds of general formula (I) wherein $R_1$, $R_3$, X and Z are as defined in formula (I) and the bond between carbon atoms 22 and 23 is a double bond
A.137 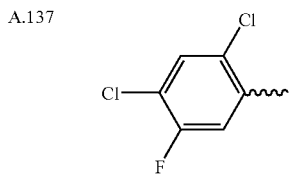
A.138 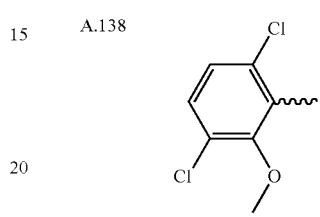
A.139 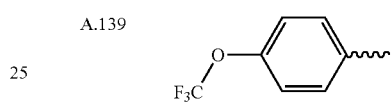
A.140 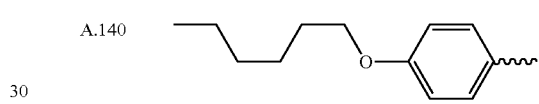
A.141 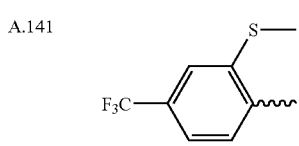
A.142 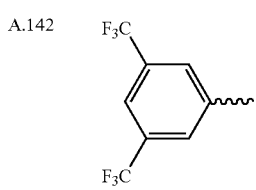
A.143 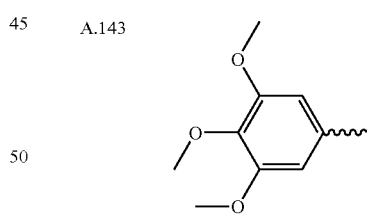
A.144 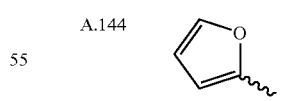
A.145 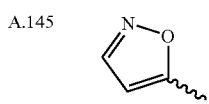
A.146 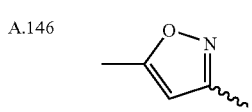

TABLE A-continued

Compounds of general formula (I) wherein $R_1$, $R_3$, X and Z are as defined in formula (I) and the bond between carbon atoms 22 and 23 is a double bond

| | |
|---|---|
| A.147 | thiophen-2-yl |
| A.148 | 3,5-dimethylisoxazol-4-yl |
| A.149 | 4-methyl-1,2,3-thiadiazol-5-yl |
| A.150 | 4-methyl-1,2,5-thiadiazol-3-yl |
| A.151 | 5-nitrofuran-2-yl |
| A.152 | 5-tert-butylfuran-2-methyl |
| A.153 | 3-tert-butyl-1-methyl-1H-pyrazol-5-yl |
| A.154 | 4-chloro-1-methyl-3-(trifluoromethyl)-1H-pyrazol-5-yl |
| A.155 | 5-methyl-2-(trifluoromethyl)furan-3-yl |
| A.156 | methoxyimino-cyano |
| A.157 | ethoxyimino-cyano |
| A.158 | 2-chloropyridin-3-yl |
| A.159 | 2-chloropyridin-4-yl |
| A.160 | 2-chloro-6-methylpyridin-4-yl |
| A.161 | 2,6-dichloropyridin-4-yl |
| A.162 | 2,5-dichloropyridin-3-yl |
| A.163 | benzofuran-2-yl |
| A.164 | benzo[c]thiophen-1-yl |
| A.165 | benzo[b]thiophen-2-yl |
| A.166 | 3-chlorobenzo[b]thiophen-2-yl |
| A.167 | 6-chlorobenzo[c]thiophen-1-yl |

TABLE A-continued

Compounds of general formula (I) wherein R₁, R₃, X and Z are as defined in formula (I) and the bond between carbon atoms 22 and 23 is a double bond

| | |
|---|---|
| A.168 | 7-methyl-2-methyl-2H-indazole |
| A.169 | naphthalen-1-yl |
| A.170 | naphthalen-2-yl |
| A.171 | naphthalen-2-yl |
| A.172 | biphenyl-4-yl |
| A.173 | Cl-CH₂-CH₂-CH₂- |
| A.174 | ethoxycarbonyl-CH₂- |
| A.175 | ethoxycarbonyl-CH(CH₃)- |
| A.176 | 4-bromo-α-methylbenzyl |
| A.177 | α-methylbenzyl |
| A.178 | benzyl |
| A.179 | (C₂H₅O)₃Si—CH₂—CH₂—CH₂— |
| A.180 | CCl₃— |
| A.181 | Cl₃C-C(=O)- |
| A.182 | isopropyl-CH-C(=O)-O- |
| A.183 | 2,5-dimethoxybenzoyl |

Table 2: Compounds of formula (I) wherein R₁ is sec-butyl (B1a) or iso-propyl (B1b), Z is —C(=O), X is a bond and R₃ is hydrogen, and the substituent R₂ for a compound corresponds to any one of lines A.1 to A.183 of Table A.

Table 3: Compounds of formula (I) wherein R₁ is sec-butyl (B1a) or iso-propyl (B1b), Z is —C(=O), X is a bond and R₃ is methyl, and the substituent R₂ for a compound corresponds to any one of lines A.1 to A.183 of Table A.

Table 4: Compounds of formula (I) wherein R₁ is sec-butyl (B1a) or iso-propyl (B1b), Z is —C(=O), X is a bond and R₃ is ethyl, and the substituent R₂ for a compound corresponds to any one of lines A.1 to A.183 of Table A.

Table 5: Compounds of formula (I) wherein R₁ is sec-butyl (B1a) or iso-propyl (B1b), Z is —C(=O), X is a bond and R₃ is n-propyl, and the substituent R₂ for a compound corresponds to any one of lines A.1 to A.183 of Table A.

Table 6: Compounds of formula (I) wherein R₁ is sec-butyl (B1a) or iso-propyl (B1b), Z is —C(=S), X is a bond and R₃ is hydrogen, and the substituent R₂ for a compound corresponds to any one of lines A.1 to A.183 of Table A.

Table 7: Compounds of formula (I) wherein R₁ is sec-butyl (B1a) or iso-propyl (B1b), Z is —C(=S), X is a bond and R₃ is methyl, and the substituent R₂ for a compound corresponds to any one of lines A.1 to A.183 of Table A.

Table 8: Compounds of formula (I) wherein R₁ is sec-butyl (B1a) or iso-propyl (B1b), Z is —C(=O), X is NH and R₃ is hydrogen, and the substituent R₂ for a compound corresponds to any one of lines A.1 to A.183 of Table A.

Table 9: Compounds of formula (I) wherein R₁ is sec-butyl (B1a) or iso-propyl (B1b), Z is —C(=O), X is NH and R₃ is methyl, and the substituent R₂ for a compound corresponds to any one of lines A.1 to A.183 of Table A.

Table 10: Compounds of formula (I) wherein R₁ is sec-butyl (B1a) or iso-propyl (B1b), Z is —C(=S), X is O and R₃ is hydrogen, and the substituent R₂ for a compound corresponds to any one of lines A.1 to A.183 of Table A.

Table 11: Compounds of formula (I) wherein R₁ is sec-butyl (B1a) or iso-propyl (B1b), Z is —C(=S), X is O and R₃ is methyl, and the substituent R₂ for a compound corresponds to any one of lines A.1 to A.183 of Table A.

Table 12: Compounds of formula (I) wherein R₁ is sec-butyl (B1a) or iso-propyl (B1b), Z is —C(=O), X is O and R₃ is hydrogen, and the substituent R₂ for a compound corresponds to any one of lines A.1 to A.183 of Table A.

Table 13: Compounds of formula (I) wherein R₁ is sec-butyl (B1a) or iso-propyl (B1b), Z is —C(=O), X is O and R₃ is methyl, and the substituent R₂ for a compound corresponds to any one of lines A.1 to A.183 of Table A.

Table 14: Compounds of formula (I) wherein $R_1$ is sec-butyl (B1a) or iso-propyl (B1b), Z is —C(=S), X is NH and $R_3$ is hydrogen, and the substituent $R_2$ for a compound corresponds to any one of lines A.1 to A.183 of Table A.

Table 15: Compounds of formula (I) wherein $R_1$ is sec-butyl (B1a) or iso-propyl (B1b), Z is —C(=S), X is NH and $R_3$ is methyl, and the substituent $R_2$ for a compound corresponds to any one of lines A.1 to A.183 of Table A.

Table 16: Compounds of formula (I) wherein $R_1$ is sec-butyl (B1a) or iso-propyl (B1b), Z is —S(=O)$_2$—, X is a bond and $R_3$ is hydrogen, and the substituent $R_2$ for a compound corresponds to any one of lines A.1 to A.183 of Table A.

Table 17: Compounds of formula (I) wherein $R_1$ is sec-butyl (B1a) or iso-propyl (B1b), Z is —S(=O)$_2$—, X is a bond and $R_3$ is methyl, and the substituent $R_2$ for a compound corresponds to any one of lines A.1 to A.183 of Table A.

Table 18: Compounds of formula (I) wherein $R_1$ is sec-butyl (B1a) or iso-propyl (B1b), Z is —S(=O)$_2$—, X is a bond and $R_3$ is ethyl, and the substituent $R_2$ for a compound corresponds to any one of lines A.1 to A.183 of Table A.

Table 19: Compounds of formula (I) wherein $R_1$ is sec-butyl (B1a) or iso-propyl (B1b), Z is —S(=O)$_2$—, X is NH and $R_3$ is hydrogen, and the substituent $R_2$ for a compound corresponds to any one of lines A.1 to A.183 of Table A.

Table 20: Compounds of formula (I) wherein $R_1$ is sec-butyl (B1a) or iso-propyl (B1b), Z is —S(=O)$_2$—, X is NCH$_3$ and $R_3$ is methyl, and the substituent $R_2$ for a compound corresponds to any one of lines A.1 to A.183 of Table A.

Table 21: Compounds of formula (I) wherein $R_1$ is sec-butyl (B1a) or iso-propyl (B1b), Z is —C(=O)—, X is S, $R_3$ is H, and the substituent $R_2$ for a compound corresponds to any one of lines A.1 to A.183 of Table A.

Table 22: Compounds of formula (I) wherein $R_1$ is sec-butyl (B$_1$a) or iso-propyl (B1b), Z is —C(=O)—, X is S, $R_3$ is methyl, and the substituent $R_2$ for a compound corresponds to any one of lines A.1 to A.183 of Table A.

Table 23: Compounds of formula (I) wherein $R_1$ is sec-butyl (B1a) or iso-propyl (B1b), Z is —C(=O)—, X is NCH$_3$, $R_3$ is H, and the substituent $R_2$ for a compound corresponds to any one of lines A.1 to A.183 of Table A.

Table 24: Compounds of formula (I) wherein $R_1$ is sec-butyl (B1a) or iso-propyl (B1b), Z is —C(=O)—, X is NCH$_3$, $R_3$ is methyl, and the substituent $R_2$ for a compound corresponds to any one of lines A.1 to A.183 of Table A.

Table 25: Compounds of formula (1) wherein $R_1$ is cyclohexyl, Z is C(=O), X is a bond and $R_3$ is hydrogen, and the substituent $R_2$ for a compound corresponds to any one of lines A.1 to A.183 of Table A.

Table 26: Compounds of formula (I) wherein $R_1$ is cyclohexyl, Z is —C(=O), X is a bond and $R_3$ is methyl, and the substituent $R_2$ for a compound corresponds to any one of lines A.1 to A.183 of Table A.

Table 27: Compounds of formula (I) wherein $R_1$ is cyclohexyl, Z is —C(=O), X is a bond and $R_3$ is ethyl, and the substituent $R_2$ for a compound corresponds to any one of lines A.1 to A.183 of Table A.

Table 28: Compounds of formula (I) wherein $R_1$ is cyclohexyl, Z is —C(=O), X is a bond and $R_3$ is n-propyl, and the substituent $R_2$ for a compound corresponds to any one of lines A.1 to A.183 of Table A.

Table 29: Compounds of formula (I) wherein $R_1$ is cyclohexyl, Z is C(=S), X is a bond and $R_3$ is hydrogen, and the substituent $R_2$ for a compound corresponds to any one of lines A.1 to A.183 of Table A.

Table 30: Compounds of formula (I) wherein $R_1$ is cyclohexyl, Z is —C(=S), X is a bond and $R_3$ is methyl, and the substituent $R_2$ for a compound corresponds to any one of lines A.1 to A.183 of Table A.

Table 31: Compounds of formula (I) wherein $R_1$ is cyclohexyl, Z is —C(=O), X is NH and $R_3$ is hydrogen, and the substituent $R_2$ for a compound corresponds to any one of lines A.1 to A.183 of Table A.

Table 32: Compounds of formula (I) wherein $R_1$ is cyclohexyl, Z is —C(=O), X is NH and $R_3$ is methyl, and the substituent $R_2$ for a compound corresponds to any one of lines A.1 to A.183 of Table A.

Table 33: Compounds of formula (I) wherein $R_1$ is cyclohexyl, Z is —C(=S), X is O and $R_3$ is hydrogen, and the substituent $R_2$ for a compound corresponds to any one of lines A.1 to A.183 of Table A.

Table 34: Compounds of formula (I) wherein $R_1$ is cyclohexyl, Z is —C(=S), X is O and $R_3$ is methyl, and the substituent $R_2$ for a compound corresponds to any one of lines A.1 to A.183 of Table A.

Table 35: Compounds of formula (I) wherein $R_1$ is cyclohexyl, Z is —C(=O), X is O and $R_3$ is hydrogen, and the substituent $R_2$ for a compound corresponds to any one of lines A.1 to A.183 of Table A.

Table 36: Compounds of formula (I) wherein $R_1$ is cyclohexyl, Z is —C(=O), X is O and $R_3$ is methyl, and the substituent $R_2$ for a compound corresponds to any one of lines A.1 to A.183 of Table A.

Table 37: Compounds of formula (I) wherein $R_1$ is cyclohexyl, Z is —C(=S), X is NH and $R_3$ is hydrogen, and the substituent $R_2$ for a compound corresponds to any one of lines A.1 to A.183 of Table A.

Table 38: Compounds of formula (I) wherein $R_1$ is cyclohexyl, Z is —C(=S), X is NH and $R_3$ is methyl, and the substituent $R_2$ for a compound corresponds to any one of lines A.1 to A.183 of Table A.

Table 39: Compounds of formula (I) wherein $R_1$ is cyclohexyl, Z is —S(=O)$_2$—, X is a bond and $R_3$ is hydrogen, and the substituent $R_2$ for a compound corresponds to any one of lines A.1 to A.183 of Table A.

Table 40: Compounds of formula (I) wherein $R_1$ is cyclohexyl, Z is —S(=O)$_2$—, X is a bond and $R_3$ is methyl, and the substituent $R_2$ for a compound corresponds to any one of lines A.1 to A.183 of Table A.

Table 41: Compounds of formula (I) wherein $R_1$ is cyclohexyl, Z is —S(=O)$_2$—, X is a bond and $R_3$ is ethyl, and the substituent $R_2$ for a compound corresponds to any one of lines A.1 to A.183 of Table A.

Table 42: Compounds of formula (I) wherein $R_1$ is cyclohexyl, Z is —S(=O)$_2$—, X is NH and $R_3$ is hydrogen, and the substituent $R_2$ for a compound corresponds to any one of lines A.1 to A.183 of Table A.

Table 43: Compounds of formula (I) wherein $R_1$ is cyclohexyl, Z is —S(=O)$_2$—, X is NCH$_3$ and $R_3$ is methyl, and the substituent $R_2$ for a compound corresponds to any one of lines A.1 to A.183 of Table A.

Table 44: Compounds of formula (I) wherein $R_1$ is cyclohexyl, Z is —C(=O)—, X is S, $R_3$ is H, and the substituent $R_2$ for a compound corresponds to any one of lines A.1 to A.183 of Table A.

Table 45: Compounds of formula (I) wherein $R_1$ is cyclohexyl, Z is —C(=O)—, X is S, $R_3$ is methyl, and the substituent $R_2$ for a compound corresponds to any one of lines A.1 to A.183 of Table A.

Table 46: Compounds of formula (I) wherein $R_1$ is cyclohexyl, Z is —C(=O)—, X is NCH$_3$, $R_3$ is H, and the substituent $R_2$ for a compound corresponds to any one of lines A.1 to A.183 of Table A.

Table 47: Compounds of formula (I) wherein $R_1$ is cyclohexyl, Z is —C(=O)—, X is NCH$_3$, $R_3$ is CH$_3$, and the substituent $R_2$ for a compound corresponds to any one of lines A.1 to A.183 of Table A.

Table 48: Compounds of formula (I) wherein $R_1$ is 1-methyl-butyl, Z is —C(=O), X is a bond and $R_3$ is hydrogen, and the substituent $R_2$ for a compound corresponds to any one of lines A.1 to A.183 of Table A.

Table 49: Compounds of formula (I) wherein $R_1$ is 1-methyl-butyl, Z is —C(=O), X is a bond and $R_3$ is methyl, and the substituent $R_2$ for a compound corresponds to any one of lines A.1 to A.183 of Table A.

Table 50: Compounds of formula (I) wherein $R_1$ is 1-methyl-butyl, Z is —C(=O), X is a bond and $R_3$ is ethyl, and the substituent $R_2$ for a compound corresponds to any one of lines A.1 to A.183 of Table A.

Table 51: Compounds of formula (I) wherein $R_1$ is 1-methyl-butyl, Z is —C(=O), X is a bond and $R_3$ is n-propyl, and the substituent $R_2$ for a compound corresponds to any one of lines A.1 to A.183 of Table A.

Table 52: Compounds of formula (I) wherein $R_1$ is 1-methyl-butyl, Z is —C(=S), X is a bond and $R_3$ is hydrogen, and the substituent $R_2$ for a compound corresponds to any one of lines A.1 to A.183 of Table A.

Table 53: Compounds of formula (I) wherein $R_1$ is 1-methyl-butyl, Z is —C(=S), X is a bond and $R_3$ is methyl, and the substituent $R_2$ for a compound corresponds to any one of lines A.1 to A.183 of Table A.

Table 54: Compounds of formula (I) wherein $R_1$ is 1-methyl-butyl, Z is —O(=O), X is NH and $R_3$ is hydrogen, and the substituent $R_2$ for a compound corresponds to any one of lines A.1 to A.183 of Table A.

Table 55: Compounds of formula (I) wherein $R_1$ is 1-methyl-butyl, Z is —C(=O), X is NH and $R_3$ is methyl, and the substituent $R_2$ for a compound corresponds to any one of lines A.1 to A.183 of Table A.

Table 56: Compounds of formula (I) wherein $R_1$ is 1-methyl-butyl, Z is —C(=S), X is O and $R_3$ is hydrogen, and the substituent $R_2$ for a compound corresponds to any one of lines A.1 to A.183 of Table A.

Table 57: Compounds of formula (I) wherein $R_1$ is 1-methyl-butyl, Z is —C(=S), X is O and $R_3$ is methyl, and the substituent $R_2$ for a compound corresponds to any one of lines A.1 to A.183 of Table A.

Table 58: Compounds of formula (I) wherein $R_1$ is 1-methyl-butyl, Z is —C(=O), X is O and $R_3$ is hydrogen, and the substituent $R_2$ for a compound corresponds to any one of lines A.1 to A.183 of Table A.

Table 59: Compounds of formula (I) wherein $R_1$ is 1-methyl-butyl, Z is —C(=O), X is O and $R_3$ is methyl, and the substituent $R_2$ for a compound corresponds to any one of lines A.1 to A.183 of Table A.

Table 60: Compounds of formula (I) wherein $R_1$ is 1-methyl-butyl, Z is —C(=S), X is NH and $R_3$ is hydrogen, and the substituent $R_2$ for a compound corresponds to any one of lines A.1 to A.183 of Table A.

Table 61: Compounds of formula (I) wherein $R_1$ is 1-methyl-butyl, Z is —C(=S), X is NH and $R_3$ is methyl, and the substituent $R_2$ for a compound corresponds to any one of lines A.1 to A.183 of Table A.

Table 62: Compounds of formula (I) wherein $R_1$ is 1-methyl-butyl, Z is —S(=O)$_2$—, X is a bond and $R_3$ is hydrogen, and the substituent $R_2$ for a compound corresponds to any one of lines A.1 to A.183 of Table A.

Table 63: Compounds of formula (I) wherein $R_1$ is 1-methyl-butyl, Z is —S(=O)$_2$—, X is a bond and $R_3$ is methyl, and the substituent $R_2$ for a compound corresponds to any one of lines A.1 to A.183 of Table A.

Table 64: Compounds of formula (I) wherein $R_1$ is 1-methyl-butyl, Z is —S(=O)$_2$—, X is a bond and $R_3$ is ethyl, and the substituent $R_2$ for a compound corresponds to any one of lines A.1 to A.183 of Table A.

Table 65: Compounds of formula (I) wherein $R_1$ is 1-methyl-butyl, Z is —S(=O)$_2$—, X is NH and $R_3$ is hydrogen, and the substituent $R_2$ for a compound corresponds to any one of lines A.1 to A.183 of Table A.

Table 66: Compounds of formula (I) wherein $R_1$ is 1-methyl-butyl, Z is —S(=O)$_2$—, X is NCH$_3$ and $R_3$ is methyl, and the substituent $R_2$ for a compound corresponds to any one of lines A.1 to A.183 of Table A.

Table 67: Compounds of formula (I) wherein R. is 1-methyl-butyl, Z is —C(=O)—, X is S, $R_3$ is H, and the substituent $R_2$ for a compound corresponds to any one of lines A.1 to A.183 of Table A.

Table 68: Compounds of formula (I) wherein $R_1$ is 1-methyl-butyl, Z is —C(=O)—, X is S, $R_3$ is methyl, and the substituent $R_2$ for a compound corresponds to any one of lines A.1 to A.183 of Table A.

Table 69: Compounds of formula (I) wherein $R_1$ is 1-methyl-butyl, Z is —C(=O)—, X is NCH$_3$, $R_3$ is H, and the substituent $R_2$ for a compound corresponds to any one of lines A.1 to A.183 of Table A.

Table 70: Compounds of formula (I) wherein $R_1$ is 1-methyl-butyl, Z is —C(=O)—, X is NCH$_3$, $R_3$ is CH$_3$, and the substituent $R_2$ for a compound corresponds to any one of lines A.1 to A.183 of Table A.

Table 71: Compounds of formula (I) wherein $R_1$ is sec-butyl (B1a) or iso-propyl (B1b), Z is C(=S), X is NCH$_3$ and $R_3$ is hydrogen, and the substituent $R_2$ for a compound corresponds to any one of lines A.1 to A.183 of Table A.

Table 72: Compounds of formula (I) wherein $R_1$ is sec-butyl (B1a) or iso-propyl (B1b), Z is —C(=S), X is NCH$_3$ and $R_3$ is methyl, and the substituent $R_2$ for a compound corresponds to any one of lines A.1 to A.183 of Table A.

Table 73: Compounds of formula (I) wherein R: is sec-butyl (B1a) or iso-propyl (B1b), Z is —C(=S), X is S and $R_3$ is hydrogen, and the substituent $R_2$ for a compound corresponds to any one of lines A.1 to A.183 of Table A.

Table 74: Compounds of formula (I) wherein $R_1$ is sec-butyl (B1a) or iso-propyl (B1b), Z is —C(=S), X is S and $R_3$ is methyl, and the substituent $R_2$ for a compound corresponds to any one of lines A.1 to A.183 of Table A.

Table 75: Compounds of formula (I) wherein $R_1$ is sec-butyl (B1a) or iso-propyl (B1b), Z is —S(=O)$_2$—, X is NH and $R_3$ is methyl, and the substituent $R_2$ for a compound corresponds to any one of lines A.1 to A.183 of Table A.

Table 76: Compounds of formula (I) wherein $R_1$ is sec-butyl (B1a) or iso-propyl (B1b), Z is —S(=O)$_2$—, X is NCH$_3$ and $R_3$ is H, and the substituent $R_2$ for a compound corresponds to any one of lines A.1 to A.183 of Table A.

Table 77: Compounds of formula (I) wherein $R_1$ is cyclohexyl, Z is —C(=S), X is NCH$_3$ and $R_3$ is hydrogen, and the substituent $R_2$ for a compound corresponds to any one of lines A.1 to A.183 of Table A.

Table 78: Compounds of formula (I) wherein $R_1$ is cyclohexyl, Z is —C(=S), X is NCH$_3$ and $R_3$ is methyl, and the substituent $R_2$ for a compound corresponds to any one of lines A.1 to A.183 of Table A.

Table 79: Compounds of formula (I) wherein $R_1$ is cyclohexyl, Z is —C(=S), X is S and $R_3$ is hydrogen, and the substituent $R_2$ for a compound corresponds to any one of lines A.1 to A.183 of Table A.

Table 80: Compounds of formula (I) wherein $R_1$ is cyclohexyl, Z is —C(=S), X is S and $R_3$ is methyl, and the substituent $R_2$ for a compound corresponds to any one of lines A.1 to A.183 of Table A.

Table 81: Compounds of formula (I) wherein $R_1$ is cyclohexyl, Z is —S(=O)$_2$—, X is NH and $R_3$ is methyl, and the substituent $R_2$ for a compound corresponds to any one of lines A.1 to A.183 of Table A.

Table 82: Compounds of formula (I) wherein $R_1$ is cyclohexyl, Z is —S(=O)$_2$—, X is NCH$_3$ and $R_3$ is H, and the substituent $R_2$ for a compound corresponds to any one of lines A.1 to A.183 of Table A.

Table 83: Compounds of formula (I) wherein R. is 1-methyl-butyl, Z is —C(=S), X is NCH$_3$ and R$_3$ is hydrogen, and the substituent R$_2$ for a compound corresponds to any one of lines A.1 to A.183 of Table A.

Table 84: Compounds of formula (I) wherein R$_1$ is 1-methyl-butyl, Z is —C(=S), X is NCH$_3$ and R$_3$ is methyl, and the substituent R$_2$ for a compound corresponds to any one of lines A.1 to A.183 of Table A.

Table 85: Compounds of formula (I) wherein R$_1$ is 1-methyl-butyl, Z is —C(=S), X is S and R$_3$ is hydrogen, and the substituent R$_2$ for a compound corresponds to any one of lines A.1 to A.183 of Table A.

Table 86: Compounds of formula (I) wherein R$_1$ is 1-methyl-butyl, Z is —C(=S), X is S and R$_3$ is methyl, and the substituent R$_2$ for a compound corresponds to any one of lines A.1 to A.183 of Table A.

Table 87: Compounds of formula (I) wherein R. is 1-methyl-butyl, Z is —S(=O)$_2$—, X is NH and R$_3$ is methyl, and the substituent R$_2$ for a compound corresponds to any one of lines A.1 to A.183 of Table A.

Table 88: Compounds of formula (I) wherein R$_1$ is 1-methyl-butyl, Z is —S(=O)$_2$—, X is NCH$_3$ and R$_3$ is H, and the substfuent R$_2$ for a compound corresponds to any one of lines A.1 to A.183 of Table A.

Table 89: Compounds of tables 2 to 88, wherein the bond between carbon atoms 22 and 23 is a single bond.

TABLE B

Compounds of general formula (I) wherein R$_1$, R$_3$ and Z are as defined in formula (I) and the bond between carbon atoms 22 and 23 is a double bond.

| No. | R$_2$ R$_4$ |
|---|---|
| B.1 | —CH$_2$CH$_2$CH$_2$— |
| B.2 | —CH$_2$(CH$_2$)$_2$CH$_2$— |
| B.3 | —CH$_2$(CH$_2$)$_3$CH$_2$— |
| B.4 | —CH$_2$CH$_2$OCH$_2$CH$_2$— |
| B.5 | —CH$_2$CH(CH$_3$)OCH(CH$_3$)CH$_2$— |
| B.6 | —CH$_2$CH$_2$SCH$_2$CH$_2$— |
| B.7 | —CH$_2$CH$_2$NHCH$_2$CH$_2$— |
| B.8 | —CH$_2$CH$_2$N(CH$_3$)CH$_2$CH$_2$— |

Table 90: Compounds of formula (I) wherein R$_1$ is sec-butyl (B1a) or iso-propyl (B1b), Z is —C(=O)—, X is N, R$_3$ is H, and the substituents R$_2$ and R$_4$ for a compound correspond to any one of lines B.1 to B.8 of Table B.

Table 91: Compounds of formula (I) wherein R$_1$ is sec-butyl (B1a) or iso-propyl (B1b), Z is —C(=O)—, X is N, R$_3$ is CH$_3$, and the substituents R$_2$ and R$_4$ for a compound correspond to any one of lines B.1 to B.8 of Table B.

Table 92: Compounds of formula (I) wherein R$_1$ is sec-butyl (B1a) or iso-propyl (B1b), Z is —C(=S)—, X is N, R$_3$ is H and the substituents R$_2$ and R$_4$ for a compound correspond to any one of lines B.1 to B.8 of Table B.

Table 93: Compounds of formula (I) wherein R$_1$ is sec-butyl (B1a) or iso-propyl (B1b), Z is —C(=S)—, X is N, R$_3$ is CH$_3$ and the substituents R$_2$ and R$_4$ for a compound correspond to any one of lines B.1 to B.8 of Table B.

Table 94: Compounds of formula (I) wherein R$_1$ is sec-butyl (B1a) or iso-propyl (B1b), Z is SO$_2$, X is N, R$_3$ is H and the substituents R$_2$ and R$_4$ for a compound correspond to any one of lines B.1 to B.8 of Table B.

Table 95: Compounds of formula (I) wherein R$_1$ is sec-butyl (B1a) or iso-propyl (B1b), Z is SO$_2$, X is N, R$_3$ is CH$_3$ and the substituents R$_2$ and R$_4$ for a compound correspond to any one of lines B.1 to B.8 of Table B.

Table 96: Compounds of formula (I) wherein R$_1$ is cyclohexyl, Z is —C(=O)—, X is N, R$_3$ is H, and the substituents R$_2$ and R$_4$ for a compound correspond to any one of lines B.1 to B.8 of Table B.

Table 97: Compounds of formula (I) wherein R$_1$ is cyclohexyl, Z is —C(=O)—, X is N, R$_3$ is CH$_3$, and the substituents R$_2$ and R$_4$ for a compound correspond to any one of lines B.1 to B.8 of Table B.

Table 98: Compounds of formula (I) wherein R$_1$ is cyclohexyl, Z is —C(=S)—, X is N, R$_3$ is H and the substituents R$_2$ and R$_4$ for a compound correspond to any one of lines B.1 to B.8 of Table B.

Table 99: Compounds of formula (I) wherein R$_1$ is cyclohexyl, Z is —C(=S)—, X is N, R$_3$ is CH$_3$ and the substituents R$_2$ and R$_4$ for a compound correspond to any one of lines B.1 to B.8 of Table B.

Table 100: Compounds of formula (I) wherein R$_1$ is cyclohexyl, Z is SO$_2$, X is N, R$_3$ is H and the substituents R$_2$ and R$_4$ for a compound correspond to any one of lines B.1 to B.8 of Table B.

Table 101: Compounds of formula (I) wherein R$_1$ is cyclohexyl, Z is SO$_2$, X is N, R$_3$ is CH$_3$ and the substituents R$_2$ and R$_4$ for a compound correspond to any one of lines B.1 to B.8 of Table B.

Table 102: Compounds of formula (I) wherein R$_1$ is 1-methyl-butyl, Z is —C(=O)—, X is N, R$_3$ is H, and the substituents R$_2$ and R$_4$ for a compound correspond to any one of lines B.1 to B.8 of Table B.

Table 103: Compounds of formula (I) wherein R$_1$ is 1-methyl-butyl, Z is —C(=O)—, X is N, R$_3$ is CH$_3$, and the substituents R$_2$ and R$_4$ for a compound correspond to any one of lines B.1 to B.8 of Table B.

Table 104: Compounds of formula (I) wherein R. is 1-methyl-butyl, Z is —C(=S)—, X is N, R$_3$ is H and the substituents R$_2$ and R$_4$ for a compound correspond to any one of lines B.1 to B.8 of Table B.

Table 105: Compounds of formula (I) wherein R$_1$ is 1-methyl-butyl, Z is —C(=S)—, X is N, R$_3$ is CH$_3$ and the substituents R$_2$ and R$_4$ for a compound correspond to any one of lines B.1 to B.8 of Table B.

Table 106: Compounds of formula (I) wherein R$_1$ is 1-methyl-butyl, Z is SO$_2$, X is N, R$_3$ is H and the substituents R$_2$ and R$_4$ for a compound correspond to any one of lines B.1 to B.8 of Table B.

Table 107: Compounds of formula (I) wherein R. is 1-methyl-butyl, Z is SO$_2$, X is N, R$_3$ is CH$_3$ and the substituents R$_2$ and R$_4$ for a compound correspond to any one of lines B.1 to B.8 of Table B.

Table 108: Compounds of tables 72 to 89, wherein the bond between carbon atoms 22 and 23 is a single bond.

Formulation Examples for use in crop protection (%=percent by weight)

| Example F1: Emulsifiable concentrates | a) | b) | c) |
|---|---|---|---|
| active ingredient | 25% | 40% | 50% |
| calcium dodecylbenzenesulfonate | 5% | 8% | 6% |
| castor oil polyethylene glycol ether (36 mol EG) | 5% | — | — |
| tributylphenol polyethylene glycol ether (30 mol EO) | — | 12% | 4% |
| cyclohexanone | — | 15% | 20% |
| xylene mixture | 65% | 25% | 20% |
| Mixing finely ground active ingredient and additives gives an emulsifiable concentrate which yields emulsions of the desired concentration on dilution with water. | | | |

-continued

| Example F2: Solutions | a) | b) | c) | d) |
|---|---|---|---|---|
| active ingredient | 80% | 10% | 5% | 95% |
| ethylene glycol monomethyl ether | — | 20% | — | — |
| polyethylene glycol (mol. wt. 400) | — | — | 70% | — |
| N-methylpyrrolid-2-one | 20% | — | — | — |
| epoxidised coconut oil | — | — | — | 1% |
| benzine (boiling range: 160-190□) | — | — | 94% | — |

Mixing finely ground active ingredient and additives gives a solution suitable for use in the form of microdrops.

| Example F3: Granules | a) | b) | c) | d) |
|---|---|---|---|---|
| active ingredient | 5% | 10% | 8% | 21% |
| kaolin | 94% | — | 79% | 54% |
| highly dispersed silicic acid | 1% | — | 13% | 7% |
| attapulgite | — | 90% | — | 18% |

The active ingredient is dissolved in dichloromethane, the solution is sprayed onto the carrier mixture and the solvent is evaporated off in vacuo.

| Example F4: Wettable powders | a) | b) | c) |
|---|---|---|---|
| active ingredient | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7-8 mol EO) | — | 2% | — |
| highly dispersed silicic acid | 5% | 10% | 10% |
| kaolin | 62% | 27% | — |

Active ingredient and additives are mixed together and the mixture is ground in a suitable mill, yielding wettable powders that can be diluted with water to form suspensions of the desired concentration.

| Example F5: Emulsifiable concentrate | |
|---|---|
| active ingredient | 10% |
| octylphenol polyethylene glycol ether (4-5 mol EO) | 3% |
| calcium dodecylbenzenesulfonate | 3% |
| castor oil polyethylene glycol ether (36 mol EO) | 4% |
| cyclohexanone | 30% |
| xylene mixture | 50% |

Mixing finely ground active ingredient and additives gives an emulsifiable concentrate which yields emulsions of the desired concentration on dilution with water.

| Example F6: Extruder granules | |
|---|---|
| active ingredient | 10% |
| sodium lignosulfonate | 2% |
| carboxymethylcellulose | 1% |
| kaolin | 87% |

Active ingredient and additives are mixed together, the mixture is ground, moistened with water, extruded and granulated and the granules are dried in a stream of air.

| Example F7: Coated granules | |
|---|---|
| active ingredient | 3% |
| polyethylene glycol (mol. wt. 200) | 3% |
| kaolin | 94% |

Uniform application of the finely ground active ingredient to the kaolin moistened with poly-ethylene glycol in a mixer yields non-dusty coated granules.

| Example F8: Suspension concentrate | |
|---|---|
| active ingredient | 40% |
| ethylene glycol | 10% |
| nonylphenol polyethylene glycol ether (15 mol EO) | 6% |
| sodium lignosulfonate | 10% |
| carboxymethylcellulose | 1% |
| aqueous formaldehyde solution (37%) | 0.2% |
| aqueous silicone oil emulsion (75%) | 0.8% |
| water | 32% |

Mixing finely ground active ingredient and additives gives a suspension concentrate which yields suspensions of the desired concentration on dilution with water.

BIOLOGICAL EXAMPLES

Example B1

Action Against *Spodoptera littoralis*

Young soybean plants are sprayed with an aqueous emulsion spray mixture comprising 12.5 ppm of test compound and, after the spray-coating has dried, the plants are populated with 10 caterpillars of *Spodoptera littoralis* in the first stage and then placed in a plastics container. 3 days later, the percentage reduction in population and the percentage reduction in feeding damage (% activity) are determined by comparing the number of dead caterpillars and the feeding damage on the treated plants with that on untreated plants.

The compounds of the Tables exhibit good activity in this test. In particular, compounds 1.002, 1.004 and 1.005 are more than 90% effective in this test.

Example B2

Action Against *Spodoptera littoralis*. Systemic

Maize seedlings are placed in a test solution comprising 12.5 ppm of test compound. 6 days later, the leaves are cut off, placed on moist filter paper in a petri dish and infested with 12 to 15 *Spodoptera littoralis* larvae in the $L_1$ stage. 4 days later, the percentage reduction in population (% activity) is determined by comparing the number of dead caterpillars on the treated plants with that on untreated plants.

The compounds of the Tables exhibit good activity in this test. In particular, compounds 1.001 to 1.008 are more than 90% effective in this test.

Example B3

Action Against *Heliothis virescens*

30-35 eggs of *Heliothis virescens*, from 0 to 24 hours old, are placed on filter paper in a petri dish on a layer of artificial nutrient. 0.8 ml of the test solution which comprises 12.5 ppm of test compound is then pipetted onto the filter papers. Evaluation is made 6 days later. The percentage reduction in population (% activity) is determined by comparing the number of dead eggs and larvae on the treated plants with that on untreated plants. The compounds of the Tables exhibit good activity in this test. In particular, compounds 1.002, 1.004 and 1.005 are more than 90% effective in this test.

Example B4

Action Against *Plutella xylostella* Caterpillars

Young cabbage plants are sprayed with an aqueous emulsion spray mixture comprising 12.5 ppm of test compound. After the spray-coating has dried, the cabbage plants are populated with 10 caterpillars of *Plutella xylostella* in the first stage and placed in a plastics container. Evaluation is made 3 days later. The percentage reduction in population and the percentage reduction in feeding damage (% activity) are determined by comparing the number of dead caterpillars and the feeding damage on the treated plants with that on the untreated plants.

The compounds of Table 1 exhibit good activity against *Plutella xylostella* in this test. In particular, compounds 1.002, 1.004 and 1.005 are more than 90% effective in this test.

Example B5

Action Against *Diabrotica balteata*

Maize seedlings are sprayed with an aqueous emulsion spray mixture comprising 12.5 ppm of test compound and, after the spray-coating has dried, the maize seedlings are populated with 10 *Diabrotica balteata* larvae in the second stage and then placed in a plastics container. 6 days later, the percentage reduction in population (% activity) is determined by comparing the number of dead larvae on the treated plants with that on untreated plants. The compounds of the Tables exhibit good activity in this test. In particular, compounds 1.002, 1.004 and 1.005 are more than 90% effective in this test.

Example B6

Action Against *Tetranychus urticae*

Young bean plants are populated with a mixed population of *Tetranychus urticae* and sprayed one day later with an aqueous emulsion spray mixture comprising 12.5 ppm of test compound. The plants are incubated for 6 days at 25° C. and subsequently evaluated. The percentage reduction in population (% activity) is determined by comparing the number of dead eggs, larvae and adults on the treated plants with that on untreated plants. The compounds of the Tables exhibit good activity in this test. In particular, compounds 1.002, 1.004 and 1.005 are more than 90% effective in this test.

What is claimed is:

1. A compound of formula

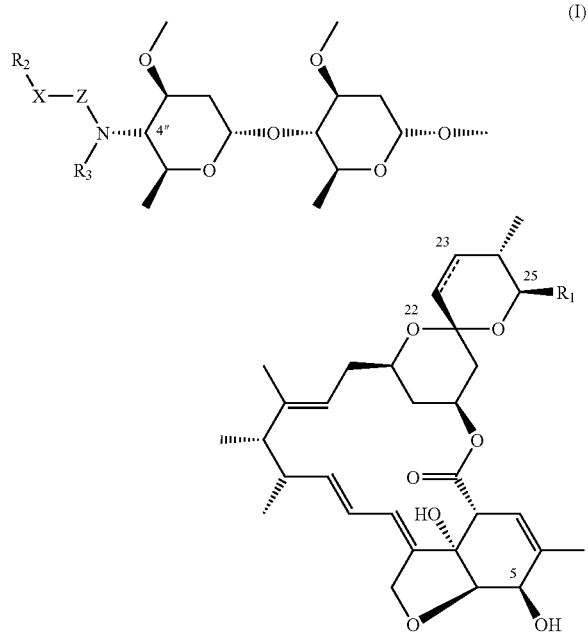

(I)

that has the S-configuration at the 4"-position and wherein the bond between carbon atoms 22 and 23 is a single or a double bond;

$R_1$ is $C_1$-$C_{12}$alkyl, $C_3$-$C_8$cycloalkyl; or $C_2$-$C_{12}$alkenyl;

$R_2$ is H, $C_2$-$C_{12}$alkenyl, $C_2$-$C_{12}$alkynyl, —C(=O)—$R_5$, aryl; wherein the $C_2$-$C_{12}$alkenyl, $C_2$-$C_{12}$alkynyl, aryl substituents may be unsubstituted or mono-to penta-substituted;

$R_3$ is H, $C_2$-$C_{12}$alkenyl or $C_2$-$C_{12}$alkynyl; wherein the $C_2$-$C_{12}$alkynyl and $C_2$-$C_{12}$alkynyl substituents may be unsubstituted or mono-to penta-substituted;

X is a bond, O, $NR_4$ or S;

Z is C=O, C=S or $SO_2$;

$R_4$ is H, $C_1$-$C_8$alkyl, $C_3$-$C_8$Cycloaklkyl, $C_2$-$C_8$alkenyl, $C_2$-$C_8$alkynyl benzyl or —C(=O)-$R_5$; or $R_2$ and $R_4$ together are a three-to seven membered alkylene or alkenylene bridge, wherein the alkylene or elkenylene bridges are unsubstituted or mono to tri-substituted; and wherein one of the methylene groups of the three-to seven membered alkylene-or alkenylene-bridge may be replaced by O, NH, S, S(=O) or $SO_2$; and wherein the substituents of the mentioned alkyl, alkeny, alkynyl, cycloalkyl, alkylene, alkenylene, aryl radicals as defined under $R_2$, $R_3$ and $R_4$ are selected from the group consisting of OH, =O, halogen, halo-$C_1$-$C_2$alkyl, CN, $NO_2$, —$N_3$, $C_3$-$C_8$cycloalkyl that is unsubstituted or substituted by from one to three methyl groups; norbornylenyl; $C_3$-$C_8$cycloalkenyl that is unsubstituted or substituted by from one to three methyl groups; $C_3$-$C_8$halocycloalkyl, $C_1$-$C_{12}$alkoxy, $C_1$-$C_6$alkoxy-$C_1$-$C_6$alkyl, $C_3$-$C_8$cycloalkoxy, $C_1$-$C_{12}$haloalkoxy, $C_1$-$C_{12}$alkythio, $C_3$-$C_8$cycloalkylthio, $C_1$-$C_{12}$haloalkylthio, $C_1$-$C_{12}$alkylsulfinyl, $C_3$-$C_8$cycloalkylsulfinyl, $C_1$-$C_{12}$haloalkylsulfinyl, $C_3$-$C_8$halocycloalkylsulfinyl, $C_1$-$C_{12}$alkylsulfonyl, $C_3$-$C_8$cycloalkylsulfonyl, $C_1$-$C_{12}$haloalkylsulfonyl, $C_3$-$C_8$halocycloalkylsulfonyl, $C_2$-$C_8$alkenyl, $C_2$-$C_8$alkynyl, NH($C_1$-$C_6$alkyl), —N($C_1$-$C_6$alkyl)$_2$, —C(=O)$R_5$, —NHC(=O)$R_6$, =NO—$C_1$-$C_6$alkyl, —P(=O)(O$C_1$-$C_6$alkyl)$_2$; aryl, pyridyl, pyrimidyl, s-triazinyl, 1,2,4-triazinyl, thienyl, furyl, tetrahydrofuranyl, pyranyl, tetrahydropyranyl, pyrrolyl, pyrazolyl, imidazolyl, thiazolyl, triazolyl, oxazolyl, thiadiazolyl, oxadiazolyl, benzothienyl, quinolinyl, quinoxalinyl, benzofuranyl, benzimidazolyl, benzopyrrolyl, benzothiazolyl, indolyl, coumarinyl, indazolyl, aryloxy; and aryl, pyridyl, pyrimidyl, s-triazinyl, 1,2,4-triazinyl, thienyl, furyl, tetrahydrofuranyl, pyranyl, tetrahydropyranyl, pyrrolyl, pyrazolyl, imidazolyl, thiazolyl, oxazolyl, thiadiazolyl, oxadiazolyl, benzothienyl, quinolinyl, quinoxalinyl, benzofuranyl, benzimidazolyl, benzopyrrolyl, benzothiazolyl, indolyl, coumarinyl, indazolyl, and aryloxy that, depending upon the possibilities of substitution at the ring, are mono- to penta-substituted by substituents selected from the group consisting of OH, =O, halogen, CN, $NO_2$, —$N_3$, $C_1$-$C_{12}$alkyl, $C_3$-$C_8$cycloalkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_6$alkoxy-$C_1$-$C_6$alkyl, dimethylamino-$C_1$-$C_6$alkoxy, $C_2$-$C_8$alkenyl, $C_2$-$C_8$alkynyl, phenoxy and phenyl-$C_1$-$C_6$alkyl; phenoxy that is unsubstituted or substituted by from one to three substituents selected independently of one another from halogen, methoxy, trifluoromethyl and trifluoromethoxy; phenyl-$C_1$-$C_6$alkoxy that is unsubstituted or substituted in the aromatic ring by from one to three substituents selected independently of one another from halogen, methoxy, trifluoromethyl and trifluoromethoxy; phenyl-$C_2$-$C_6$alkenyl, phenyl-$C_2$-$C_6$alkynyl, methylenedioxy, —C(=O)$R_5$,—O—C(=O)$R_8$, —NH—C(=O)$R_6$, $NH_2$, NH($C_1$-$C_{12}$alkyl), N($C_1C_{12}$alkyl)$_2$, $C_1$-$C_6$alkylsulfinyl, $C_3$-$C_8$cycloalkylsulfinyl, $C_1$-$C_6$haloalkylsulfinyl, $C_3$-$C_8$halocycloalkylsulfinyl, $C_1$-$C_6$alkylsulfonyl, $C_3$-$C_8$cycloalkylsulfonyl, $C_1$-$C_6$haloalkylsulfonyl and $C_3$-$C_8$halocycloalkylsulfonyl;

$R_5$ is H, OH, SH, $NH_2$, $NH(C_1$-$C_{12}$alkyl), $N(C_1$-$C_{12}$alkyl)$_2$, $C_1$-$C_{12}$alkyl, $C_3$-$C_8$cycloalkyl, $C_1$-$C_{12}$haloalkyl, $C_1$-$C_{12}$alkoxy, $C_1$-$C_{12}$haloalkoxy, $C_1$-$C_6$alkoxy-$C_1$-$C_{12}$alkoxy, $C_1$-$C_{12}$alkylthio, $C_2$-$C_8$alkenyloxy, $C_2$-$C_8$alkynyloxy; phenyl, phenoxy, benzyloxy, NH-phenyl, —N($C_1$-$C_6$alkyl)-phenyl, NH—$C_1$-$C_6$alkyl-C(=O)—$R_7$, —N($C_1$-$C_6$alkyl)-$C_1$-$C_6$alkyl-C(=O)—$R_7$; or phenyl, phenoxy, benzyloxy, NH-phenyl or —N($C_1$-$C_6$alkyl)-phenyl each of which is substituted in the aromatic ring by from one to three substituents selected independently of one another from halogen, $C_1$-$C_6$alkoxy, $C_1$-$C_6$haloalkyl and $C_1$-$C_6$haloalkoxy;

$R_6$ is H, $C_1$-$C_{12}$alkyl, $C_1$-$C_{12}$haloalkyl, $C_2$-$C_8$alkenyl, $C_2$-$C_8$alkynyl, phenyl, benzyl, $NH_2$, $NH(C_1$-$C_{12}$alkyl), $N(C_1$-$C_{12}$alkyl)$_2$, —NH-phenyl or —N($C_1$-$C_{12}$alkyl)-phenyl; and $R_7$ is H, OH, $C_1$-$C_{12}$alkyl, C,-$C_{12}$alkoxy, $C_1$-$C_6$alkoxy-$C_1$-$C_6$alkoxy, $C_2$-$C_8$alkenyloxy, phenyl, phenoxy, benzyloxy, $NH_2$, $NH(C_1$-$C_{12}$alkyl), $N(C_1$-$C_{12}$alkyl)$_2$, —NH-phenyl or —N($C_1$-$C_{12}$alkyl)-phenyl;

or, where applicable, an E/Z isomer, a mixture of E/Z isomers and/or a tautomer, in each case in free form or in salt form;

with the proviso that Z is not C=O when X is a bond, $R_2$ is H, $R_3$ is hydrogen, the bond between carbon atoms 22 and 23 is a double bond and $R_1$ is i-propyl or sec-butyl.

2. A pesticidal composition comprising as active ingredient at least one compound of formula (I) as described in claim 1, and at least one adjuvant.

3. A method of controlling pests, which comprises applying a composition as described in claim 2 to the pests or to the locus thereof.

4. A process for the preparation of a composition comprising at least one adjuvant, as described in claim 2, which comprises intimately mixing and/or grinding the active ingredient with the adjuvant(s).

5. A method according to claim 3 for protecting a plant propagation material, which comprises treating the propagation material or a planting site of the propagation material.

* * * * *

UNITED STATES PATENT AND TRADEMARK OFFICE
CERTIFICATE OF CORRECTION

PATENT NO. : 7,608,595 B2
APPLICATION NO. : 10/513247
DATED : October 27, 2009
INVENTOR(S) : Tobler et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 864 days.

Signed and Sealed this

Twelfth Day of October, 2010

David J. Kappos
*Director of the United States Patent and Trademark Office*